(12) United States Patent
Daher

(10) Patent No.: US 10,406,309 B2
(45) Date of Patent: Sep. 10, 2019

(54) ENDOBRONCHIAL TUBE WITH INTEGRATED IMAGE SENSOR AND A CLEANING NOZZLE ARRANGEMENT

(71) Applicant: ETView Ltd., Misgav (IL)

(72) Inventor: Elias Daher, Bielefeld (DE)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 13/737,944

(22) Filed: Jan. 10, 2013

(65) Prior Publication Data

US 2014/0031622 A1   Jan. 30, 2014

Related U.S. Application Data

(63) Continuation-in-part of application No. PCT/IB2012/052077, filed on Apr. 26, 2012.
(Continued)

(51) Int. Cl.
*A61B 1/12* (2006.01)
*A61M 16/04* (2006.01)
*A61B 1/00* (2006.01)
*A61B 1/267* (2006.01)
*A61B 1/012* (2006.01)
(Continued)

(52) U.S. Cl.
CPC ..... *A61M 16/0463* (2013.01); *A61B 1/00018* (2013.01); *A61B 1/00082* (2013.01); *A61B 1/00091* (2013.01); *A61B 1/00094* (2013.01); *A61B 1/00124* (2013.01); *A61B 1/012* (2013.01); *A61B 1/015* (2013.01); *A61B 1/05* (2013.01); *A61B 1/051* (2013.01); *A61B 1/0676* (2013.01); *A61B 1/0684* (2013.01); *A61B 1/07* (2013.01); *A61B 1/12* (2013.01); *A61B 1/126* (2013.01); *A61B 1/2676* (2013.01); *A61B 1/313* (2013.01); *A61M 16/0057* (2013.01); *A61M 16/04* (2013.01); *A61M 16/0404* (2014.02); *A61M 16/0434* (2013.01); *A61M 16/0459* (2014.02); *A61M 16/0461* (2013.01); *A61M 16/0465* (2013.01); *A61M 16/0486* (2014.02); *A61M 16/0488* (2013.01);
(Continued)

(58) Field of Classification Search
CPC . A61B 1/00082; A61B 1/00091; A61B 1/126; A61B 1/2676
USPC ......... 600/114–116, 120, 156–158; 604/264, 604/275–279, 295; 128/200.26, 207.14, 128/207.15
See application file for complete search history.

(56) References Cited

U.S. PATENT DOCUMENTS

| 543,616 A | 7/1895 | Dow |
| 1,246,339 A | 11/1917 | Smit |

(Continued)

FOREIGN PATENT DOCUMENTS

| CN | 201862108 | 6/2011 |
| DE | 4132687 A1 | 4/1993 |

(Continued)

OTHER PUBLICATIONS

ISR for PCT/IL2003/000797 dated Oct. 3, 2003.
(Continued)

*Primary Examiner* — Matthew J Kasztejna
(74) *Attorney, Agent, or Firm* — Faegre Baker Daniels LLP

(57) ABSTRACT

An endobronchial tube which contains an integrated camera and light source and a cleaning nozzle arrangement disposed within dedicated peripheral lumen within the tube's wall.

16 Claims, 12 Drawing Sheets

Related U.S. Application Data

(60) Provisional application No. 61/506,210, filed on Jul. 11, 2011.

(51) Int. Cl.

| | | |
|---|---|---|
| *A61B 1/05* | (2006.01) | |
| *A61B 1/06* | (2006.01) | |
| *A61B 1/07* | (2006.01) | |
| *A61B 1/313* | (2006.01) | |
| *A61M 16/00* | (2006.01) | |
| *A61M 16/10* | (2006.01) | |
| *A61B 1/015* | (2006.01) | |
| *A61M 16/08* | (2006.01) | |
| *A61M 15/00* | (2006.01) | |

(52) U.S. Cl.
CPC ...... *A61M 16/0833* (2014.02); *A61M 16/104* (2013.01); *A61M 15/00* (2013.01)

(56) References Cited

U.S. PATENT DOCUMENTS

| | | |
|---|---|---|
| 2,797,683 A | 7/1957 | Aiken |
| 3,350,553 A | 10/1967 | Cline |
| 3,539,794 A | 11/1970 | Rauhut et al. |
| 3,576,987 A | 5/1971 | Voight et al. |
| 3,716,047 A | 2/1973 | Moore et al. |
| 3,729,425 A | 4/1973 | Andress et al. |
| 3,776,222 A | 12/1973 | Smiddy |
| 3,808,414 A | 4/1974 | Roberts |
| 3,893,938 A | 7/1975 | Rauhut |
| 4,150,676 A | 4/1979 | Jackson |
| 4,253,447 A | 3/1981 | Moore |
| 4,383,534 A | 5/1983 | Peters |
| 4,437,458 A | 3/1984 | Upsher |
| 4,509,507 A | 4/1985 | Yabe |
| 4,567,882 A | 2/1986 | Heller |
| 4,602,281 A | 7/1986 | Nagasaki et al. |
| 4,616,631 A | 10/1986 | Takahashi |
| 4,635,166 A | 1/1987 | Cameron |
| 4,643,170 A | 2/1987 | Miyazaki |
| 4,742,819 A | 5/1988 | George |
| 4,759,346 A | 7/1988 | Nakajima |
| 4,813,431 A | 3/1989 | Brown |
| 4,814,949 A | 3/1989 | Elliott |
| 4,846,153 A | 7/1989 | Berci |
| 4,877,016 A | 10/1989 | Kantor et al. |
| 4,884,133 A | 11/1989 | Kanno |
| 4,998,972 A | 3/1991 | Chin et al. |
| 5,005,573 A | 4/1991 | Buchanan |
| 5,065,755 A | 11/1991 | Klafta |
| 5,179,938 A | 1/1993 | Lonky |
| 5,193,544 A | 3/1993 | Jaffe |
| 5,207,213 A | 5/1993 | Auhll et al. |
| 5,241,170 A | 8/1993 | Field, Jr. |
| 5,241,956 A | 9/1993 | Brain |
| 5,249,571 A | 10/1993 | Brain |
| 5,282,464 A | 2/1994 | Brain |
| 5,285,778 A | 2/1994 | Mackin |
| 5,287,848 A | 2/1994 | Cubb et al. |
| 5,297,547 A | 3/1994 | Brain |
| 5,305,743 A | 4/1994 | Brain |
| 5,329,938 A | 7/1994 | Lonky |
| 5,329,940 A | 7/1994 | Adair |
| 5,348,690 A | 9/1994 | Cohen et al. |
| 5,355,879 A | 10/1994 | Brain |
| 5,363,838 A | 11/1994 | George |
| 5,373,317 A | 12/1994 | Salvati |
| 5,400,771 A | 3/1995 | Pirak |
| 5,457,613 A | 10/1995 | Vandenbelt et al. |
| 5,488,544 A | 1/1996 | Ladyjensky |
| 5,499,625 A * | 3/1996 | Frass et al. ............ 128/207.15 |
| 5,527,261 A | 6/1996 | Monroe |
| 5,552,968 A | 9/1996 | Ladyjensky |
| 5,569,300 A | 10/1996 | Redmon |
| 5,580,147 A | 12/1996 | Salerno |
| 5,607,386 A | 3/1997 | Flam |
| 5,622,182 A | 4/1997 | Jaffe |
| 5,665,052 A | 9/1997 | Bullard |
| 5,666,222 A | 9/1997 | Ning |
| 5,676,635 A | 10/1997 | Levin |
| 5,702,351 A | 12/1997 | Bar-Or |
| 5,716,329 A | 2/1998 | Dieter |
| 5,718,666 A | 2/1998 | Alarcon |
| 5,725,476 A * | 3/1998 | Yasui et al. ................ 600/157 |
| 5,735,792 A | 4/1998 | Vanden Hoek |
| 5,775,322 A | 7/1998 | Silverstein et al. |
| 5,792,053 A | 8/1998 | Skladnev |
| 5,800,344 A | 9/1998 | Wood |
| 5,803,898 A | 9/1998 | Bashour |
| 5,819,727 A | 10/1998 | Linder |
| 5,827,178 A | 10/1998 | Berall |
| 5,873,814 A | 2/1999 | Adair |
| 5,873,818 A | 2/1999 | Rothfels |
| 5,879,304 A | 3/1999 | Shuchman |
| 5,888,195 A | 3/1999 | Schneider |
| 5,888,196 A | 3/1999 | Bonutti |
| 5,891,013 A | 4/1999 | Thompson |
| 5,904,648 A | 5/1999 | Arndt |
| 5,908,294 A | 6/1999 | Schick |
| 5,913,816 A | 6/1999 | Sanders |
| 5,941,816 A | 8/1999 | Barthel et al. |
| 5,944,654 A | 8/1999 | Crawford |
| 6,004,265 A | 12/1999 | Hsu et al. |
| 6,024,697 A | 2/2000 | Pisarik |
| 6,050,713 A | 4/2000 | O'Donnell et al. |
| 6,067,985 A | 5/2000 | Islava |
| 6,079,409 A | 6/2000 | Brain |
| 6,091,453 A | 7/2000 | Coan |
| 6,115,523 A | 9/2000 | Gravenstein |
| 6,126,592 A | 10/2000 | Proch et al. |
| 6,142,144 A | 11/2000 | Pacey |
| 6,142,935 A | 11/2000 | Flom et al. |
| 6,161,537 A | 12/2000 | Gravenstein et al. |
| 6,164,277 A | 12/2000 | Merideth |
| 6,176,824 B1 | 1/2001 | Davis |
| 6,186,944 B1 | 2/2001 | Tsai |
| 6,189,533 B1 | 2/2001 | Simon et al. |
| 6,228,025 B1 | 5/2001 | Hipps et al. |
| 6,248,060 B1 * | 6/2001 | Buess et al. ................ 600/182 |
| 6,260,994 B1 | 7/2001 | Matsumoto |
| 6,266,547 B1 | 7/2001 | Walker |
| 6,318,887 B1 | 11/2001 | Matsumoto |
| 6,322,498 B1 | 11/2001 | Gravenstein |
| 6,331,156 B1 | 12/2001 | Haefele |
| 6,419,262 B1 | 7/2002 | Fendt et al. |
| 6,419,626 B1 | 7/2002 | Yoon |
| 6,432,042 B1 | 8/2002 | Bashour |
| 6,447,446 B1 | 9/2002 | Smith et al. |
| 6,449,006 B1 | 9/2002 | Shipp |
| 6,458,076 B1 | 10/2002 | Pruitt |
| 6,478,730 B1 | 11/2002 | Bala et al. |
| 6,533,722 B2 | 3/2003 | Nakashima |
| 6,543,447 B2 | 4/2003 | Pacey |
| 6,551,240 B2 | 4/2003 | Henzler |
| 6,616,600 B2 | 9/2003 | Pauker |
| 6,628,335 B1 | 9/2003 | Numazaki |
| 6,648,816 B2 | 11/2003 | Irion |
| 6,655,377 B2 | 12/2003 | Pacey |
| 6,692,431 B2 | 2/2004 | Kazakevich |
| 6,712,760 B2 | 3/2004 | Sano et al. |
| 6,730,019 B2 | 5/2004 | Irion |
| 6,741,286 B2 | 5/2004 | Meek |
| 6,796,939 B1 | 9/2004 | Hirata et al. |
| 6,847,394 B1 | 1/2005 | Hansen |
| 6,923,176 B2 | 8/2005 | Ranzinger |
| 6,929,600 B2 | 8/2005 | Hill |
| 7,013,899 B2 | 3/2006 | Alfery |
| 7,052,456 B2 | 5/2006 | Simon |
| 7,057,639 B2 | 6/2006 | Spoonhower |
| 7,128,071 B2 | 10/2006 | Brain |
| 7,159,590 B2 | 1/2007 | Rife |
| 7,297,105 B2 | 11/2007 | Mackin |
| 7,384,308 B2 | 6/2008 | Boehnlein |

(56) References Cited

U.S. PATENT DOCUMENTS

| | | | |
|---|---|---|---|
| 7,458,375 B2 | 12/2008 | Schwartz | |
| 7,530,946 B2 | 5/2009 | Hartwick | |
| 7,584,534 B2 | 9/2009 | Pease | |
| 7,658,708 B2 | 2/2010 | Schwartz | |
| 7,758,495 B2 | 7/2010 | Pease | |
| 7,862,173 B1 | 1/2011 | Ellman | |
| 7,878,973 B2 | 2/2011 | Yee | |
| 7,938,119 B2 | 5/2011 | Chen | |
| 7,942,813 B2 | 5/2011 | Mackin | |
| 7,946,981 B1 | 5/2011 | Cubb | |
| 7,976,459 B2 | 7/2011 | Laser | |
| 8,038,606 B2 | 10/2011 | Otawara | |
| 8,042,545 B2 | 10/2011 | Schwartz | |
| 8,047,215 B1 | 11/2011 | Sasaki | |
| 8,226,571 B2 | 7/2012 | Landesberg | |
| 8,231,524 B2 | 7/2012 | Schwartz | |
| 8,413,658 B2 | 4/2013 | Williams | |
| 8,458,844 B2 | 6/2013 | Vazales | |
| 8,473,033 B2 | 6/2013 | Wood et al. | |
| 8,479,739 B2 | 7/2013 | Hirsh | |
| 8,534,287 B2 | 9/2013 | Vazales | |
| 8,584,678 B2 | 11/2013 | Pol | |
| 8,696,548 B2 | 4/2014 | Gilboa | |
| 8,696,685 B2 | 4/2014 | Gilboa | |
| 8,790,270 B2 | 7/2014 | Landesberg | |
| 8,863,746 B2 | 10/2014 | Totz | |
| 8,887,730 B2 | 11/2014 | Wood | |
| 8,932,207 B2 | 1/2015 | Greenburg | |
| 8,978,657 B2 | 3/2015 | Sandmore et al. | |
| 8,998,798 B2 | 4/2015 | Hayman | |
| 9,055,881 B2 | 6/2015 | Gilboa | |
| 9,155,854 B2 | 10/2015 | Hayman | |
| 9,204,794 B2 | 12/2015 | Lisogurski et al. | |
| 9,211,060 B2 | 12/2015 | Waldron et al. | |
| 9,242,058 B2 | 1/2016 | Hayman et al. | |
| 9,271,803 B2 | 3/2016 | Averbuch et al. | |
| 9,283,342 B1 | 3/2016 | Gardner | |
| 9,332,891 B2 | 5/2016 | Vazales | |
| 9,357,905 B2 | 6/2016 | Molnar | |
| 9,415,179 B2 | 8/2016 | Molnar | |
| 9,572,946 B2 | 2/2017 | Chun | |
| 9,579,012 B2 | 2/2017 | Vazales | |
| 9,603,515 B2 | 3/2017 | Zocca | |
| 9,662,466 B2 | 5/2017 | Gunday | |
| 9,750,913 B2 | 9/2017 | Schwartz | |
| 9,788,755 B2 | 10/2017 | Hayman | |
| 9,801,535 B2 | 10/2017 | Turnbull | |
| 9,820,642 B2 | 11/2017 | Law | |
| 9,826,892 B2 | 11/2017 | Dresher | |
| 9,854,962 B2 | 1/2018 | McGrail | |
| 9,855,111 B2 | 1/2018 | Vazales | |
| 9,888,832 B2 | 2/2018 | Schwartz | |
| 9,907,624 B2 | 3/2018 | Vazales | |
| 2001/0023312 A1 | 9/2001 | Pacey | |
| 2001/0028227 A1 | 10/2001 | Lys | |
| 2002/0007110 A1 | 1/2002 | Irion | |
| 2002/0045801 A1 | 4/2002 | Niida | |
| 2002/0062062 A1 | 5/2002 | Belson et al. | |
| 2002/0072680 A1 | 6/2002 | Williams | |
| 2002/0076280 A1 | 6/2002 | Semotiuk | |
| 2002/0077527 A1 | 6/2002 | Aydelotte | |
| 2002/0108610 A1 | 8/2002 | Christopher | |
| 2002/0120181 A1 | 8/2002 | Irion | |
| 2002/0162557 A1 | 11/2002 | Simon et al. | |
| 2002/0193664 A1 | 12/2002 | Ross et al. | |
| 2003/0011538 A1 | 1/2003 | Lys | |
| 2003/0018237 A1 | 1/2003 | Okada | |
| 2003/0028078 A1 | 2/2003 | Glukhovsky | |
| 2003/0030745 A1 | 2/2003 | Meek | |
| 2003/0035048 A1 | 2/2003 | Shipp | |
| 2003/0042493 A1 | 3/2003 | Kazakevich | |
| 2003/0050534 A1 | 3/2003 | Kazakevich | |
| 2003/0051733 A1 | 3/2003 | Kotmel et al. | |
| 2003/0078476 A1 | 4/2003 | Hill | |
| 2004/0044269 A1 | 3/2004 | Shibata | |
| 2004/0143167 A1 | 7/2004 | Branch et al. | |
| 2004/0210114 A1 | 10/2004 | Simon | |
| 2005/0039754 A1 | 2/2005 | Simon | |
| 2005/0065496 A1 | 3/2005 | Simon et al. | |
| 2005/0090712 A1 | 4/2005 | Cubb | |
| 2007/0215162 A1 | 9/2007 | Glassenberg et al. | |
| 2008/0146879 A1 | 6/2008 | Pacey | |
| 2008/0188715 A1* | 8/2008 | Fujimoto | 600/157 |
| 2008/0200764 A1* | 8/2008 | Okada | 600/157 |
| 2009/0227998 A1 | 9/2009 | Aljuri | |
| 2009/0253964 A1* | 10/2009 | Miyamoto | 600/157 |
| 2010/0113916 A1 | 5/2010 | Kumar | |
| 2010/0249639 A1 | 9/2010 | Bhatt | |
| 2011/0197888 A1 | 8/2011 | Deutsch | |
| 2011/0282148 A1 | 11/2011 | Kase et al. | |
| 2011/0313347 A1 | 12/2011 | Zocca et al. | |
| 2011/0315147 A1 | 12/2011 | Wood et al. | |
| 2012/0041534 A1 | 2/2012 | Clerc et al. | |
| 2012/0044153 A1 | 2/2012 | Clerc | |
| 2012/0065469 A1 | 3/2012 | Allyn | |
| 2012/0172664 A1* | 7/2012 | Hayman et al. | 600/109 |
| 2012/0172665 A1 | 7/2012 | Allyn | |
| 2012/0197086 A1 | 8/2012 | Morris et al. | |
| 2012/0226100 A1 | 9/2012 | Greenburg | |
| 2012/0259173 A1* | 10/2012 | Waldron et al. | 600/109 |
| 2012/0302833 A1 | 11/2012 | Hayman et al. | |
| 2013/0158351 A1* | 6/2013 | Daher et al. | 600/109 |
| 2013/0269703 A1 | 10/2013 | Wood | |
| 2013/0303849 A1 | 11/2013 | Allyn | |
| 2013/0317339 A1 | 11/2013 | Waldstreicher | |
| 2013/0324798 A1 | 12/2013 | Molnar et al. | |
| 2014/0024893 A1 | 1/2014 | Allyn | |
| 2014/0024895 A1 | 1/2014 | Allyn | |
| 2014/0033455 A1 | 2/2014 | Vazales | |
| 2014/0046142 A1 | 2/2014 | Gavriely | |
| 2014/0094651 A1 | 4/2014 | Allyn | |
| 2014/0094652 A1 | 4/2014 | Allyn | |
| 2014/0094653 A1 | 4/2014 | Allyn | |
| 2014/0128672 A1 | 5/2014 | Daher | |
| 2014/0150782 A1 | 6/2014 | Vazales et al. | |
| 2014/0221921 A1 | 8/2014 | Gilboa | |
| 2014/0309494 A1 | 10/2014 | Molnar | |
| 2015/0099927 A1 | 4/2015 | Ali | |
| 2015/0126808 A1 | 5/2015 | Roze | |
| 2015/0133741 A1 | 5/2015 | Gill | |
| 2015/0174352 A1 | 6/2015 | Hayman | |
| 2015/0190044 A1 | 7/2015 | Livnat | |
| 2015/0223668 A1 | 8/2015 | Gilboa | |
| 2015/0305596 A1 | 10/2015 | Oskin et al. | |
| 2015/0305650 A1 | 10/2015 | Hunter et al. | |
| 2016/0000303 A1 | 1/2016 | Klein et al. | |
| 2016/0030693 A1 | 2/2016 | Nakatate | |
| 2016/0038008 A1 | 2/2016 | Molnar | |
| 2016/0038014 A1 | 2/2016 | Molnar | |
| 2016/0051221 A1 | 2/2016 | Dickhans et al. | |
| 2016/0101253 A1 | 4/2016 | Alahmadi | |
| 2016/0106308 A1 | 4/2016 | Field | |
| 2016/0157708 A1 | 6/2016 | Daher | |
| 2016/0183777 A1 | 6/2016 | Daher et al. | |
| 2016/0206189 A1 | 7/2016 | Nearman | |
| 2016/0227991 A1 | 8/2016 | Hayut | |
| 2016/0256646 A1 | 9/2016 | Vazales | |
| 2016/0287825 A1 | 10/2016 | Daher et al. | |
| 2017/0119494 A1 | 5/2017 | Vazales | |

FOREIGN PATENT DOCUMENTS

| | | |
|---|---|---|
| DE | 29805624 U1 | 7/1998 |
| EP | 0712601 | 5/1996 |
| GB | 2357856 A | 7/2001 |
| JP | 03258268 | 11/1991 |
| JP | 622902 | 2/1994 |
| JP | 06217933 | 8/1994 |
| JP | 8117184 A | 5/1996 |
| JP | 08126603 | 5/1996 |
| JP | 2001501843 | 2/2001 |
| JP | 2001128925 | 5/2001 |
| JP | 2002508982 | 3/2002 |
| JP | 2002514947 | 5/2002 |

(56) References Cited

FOREIGN PATENT DOCUMENTS

| JP | 2009505721 | | 2/2009 |
|---|---|---|---|
| JP | 2011010685 | | 1/2011 |
| WO | WO2004030527 | | 4/1994 |
| WO | WO9428784 | | 12/1994 |
| WO | WO9729679 | | 8/1997 |
| WO | WO9814112 | | 4/1998 |
| WO | WO9935960 | | 7/1999 |
| WO | 1999045990 | A1 | 9/1999 |
| WO | WO200054655 | A1 | 9/2000 |
| WO | WO01/56458 | | 8/2001 |
| WO | WO0154565 | | 8/2001 |
| WO | 2002056951 | A1 | 7/2002 |
| WO | WO02085194 | | 10/2002 |
| WO | 2003075979 | A2 | 9/2003 |
| WO | 2003101516 | A1 | 12/2003 |
| WO | 2004093791 | A2 | 11/2004 |
| WO | 2008103448 | A1 | 8/2008 |
| WO | 2010011781 | | 1/2010 |
| WO | 2012091859 | A1 | 7/2012 |
| WO | WO 2016004302 | | 1/2016 |

OTHER PUBLICATIONS

OA for CA 2501300 dated Aug. 30, 2011.
OA for CA 2501300 dated Dec. 3, 2010.
OA for JP 2004-541140 dated Aug. 9, 2011.
OA for JP 2004-541140 dated Jun. 16, 2010.
OA for EP 03751231.6 dated Feb. 9, 2007.
"Care of the Mechanically Ventilated Patient With a Tracheotomy". (1994) Chapter 35 p. 761-774.
Scanlan et al., "Egan's Fundamenttals of Respiratory Care", 1999, Mosby.
Minutes of the oral proceedings for EP03751231.6—dated Jan. 24, 2007.
Tobin, "Principles and Practice of Mechanical Ventilation", 1994, Artificial, Airways and Managment. Part X p. 698-729.
OA for EP 03751231.6 dated Oct. 17, 2006.
OA for EP 03751231.6 dated Mar. 29, 2007.
OA for EP 03751231.6 dated Sep. 27, 2005.
Michael Emmanuel Leventon, "A Registration, Tracking, and Visualization System for Image-Guided Surgery"—Massachusetts Institute of Technology(May 1997).
OA for JP 2004-541140 dated Jan. 24, 2011.
ISR for PCT/IB2012/052077 dated Aug. 17, 2012.
Adair (2001). Macintosh Lighted Stylet, located at <http://www.adair.at/eng/museum/equip/acctracheal/macintoshlighted.html> last visited on Mar. 28, 2003.
Anonymous (2002). "Intubation-Advances Airway Management (#10102.)" Procedure 2 pages.
Anonymous (2003). "Anatomic Landmarks," located at <http://www.rnceus.com/resp/respthoracic.html>.
Birmingham et al. (1986). "Esophageal Intubation: A Review of Detection Techniques," Anesth. Analg. 65:886-891.
Debo, R.F. et al. (1989). "Cricoarytenoid Subluxation: Complication of Blind Intubation With a Lighted Stylet" Ear, Nose, Throat Journal vol. 68.
Dey, D. et al. (2000). "Mixed Reality of Merging of Endoscopic Images and 3-D Surfaces," 8 pages.
Graphic Solutions, Inc. (2003). Thin Flexible Battery product information sheets located at <http://www.graphicsolutionsinc.com/tfb.html> last visited on Mar. 26, 2003. 3 pages.
Heller, R.M. and Heller, T.W. (1994). "Experience With the Illuminated Endotracheal Tube in the Prevention of Unsafe Intubations in the Premature and Full-Term Newborn," Pediatrics 93(3):389-391.
Hudson RCI Brochure (No Date Available). Airway Management product sheets, pp. 1-22.

King, H.-K. (2002). "Soft-tip Intubating Stylet" Brief Communication: Acta Anaethesiol Sin 40:135-137.
Lumex, Inc. (1997-2001). T-1.88mm Stove Pipe Lens LED Lamp product sheet, located at <http://www.lumex.com/pls/lumex/subproduct.sub.—galary> last visited on Mar. 31, 2003, 1 page.
Lumex, Inc. (1997-2001). T-2mm Axial Leaded LED Lamp product sheet, located at <http://www.lumex.com/pls/lumex/subproduct.sub.—galary> last visited on Mar. 31, 2003, 2 pages.
Luxeon Dental Brochure (2002). "Power Light source" Luxeon Dental Technical Data D535, 10 pages.
Mercury Medical Catalog (No Date Available). Intubation Products, 24 pages.
Nellcor Product Brochure (2003). Hi-Lo Tracheal Tube product sheet located at <http://www.nellcor.com/prod/Product.aspx?> last visited on Mar. 27, 2003. 1 page.
Nellcor Puritan Bennett Inc. (2003). Disposable Cannula Cuffed Tracheostomy Tubes product information sheet located at <http://www.nellcor.com/prod/Product.aspx?> last visited on Mar. 27, 2003.
Nellcor Puritan Bennett Inc. (2003). Disposable Cannula Cuffless Tracheostomy Tubes Product Information sheet located at <http://www.nellcor.com.prod/Product.aspx?> last visited on Mar. 27, 2003. 1 page.
Nellcor Puritan Bennett Inc. (2003). EMT Emergency Medicine Tube Product Fact Sheet located at <http://www.nellcor.com/prod/Product.aspx> last visited on Mar. 27, 2003, 1 page.
Nellcor Puritan Bennett Inc. (2003). Laser-Flex Tracheal Tube Product Fact Sheet located at <http://www.nellcor.com/prod/Product.aspx> last visited on Mar. 27, 2003, 1 page.
Power Paper Ltd. Brochure (2003). Power Paper, Micro-Powered Devices, Thin and Flexible Batteries located at <http://www.powerpaper.com/3.sub.—technology/advantage.html> last visited on Mar. 27, 2003. 6 pages.
Quallion, LLC Product Sheet (2002). I Series Product Feature Fact Sheet, located at <http://www.quallion.com/prod.sub.—i.html> last visited on Apr. 2, 2002. 1 page.
Seiko Instruments, Inc. (2002) Micro Batteries Product Catalogue. 28 pages.
Tech:Med Brochure: Face Shields and Product Masks, pp. 21-28. (No Date Available).
ISR for PCT/US2004/011773 dated Apr. 7, 2005.
EP search report for related EP14150501 dated Jul. 2, 2014.
Machine translation of JP2011010685.
Office Action for related JP2014-519648, dated Mar. 1, 2016 (translation).
Office Action in corresponding EP application 12727168, dated Mar. 3, 2014.
Office Action for U.S. Appl. No. 14/967,048, dated Oct. 21, 2016.
Office Action for U.S. Appl. No. 13/819,743, dated Jul. 14, 2016.
Office Action for U.S. Appl. No. 13/819,743, dated Oct. 7, 2015.
Office Action for U.S. Appl. No. 13/819,743, dated Feb. 5, 2015.
Office Action for U.S. Appl. No. 14/151,846, dated Oct. 6, 2016.
Office Action for U.S. Appl. No. 14/151,846, dated Apr. 4, 2016.
Office Action for U.S. Appl. No. 14/967,048, dated Jun. 6, 2016.
Pre-Interview First Office Action for U.S. Appl. No. 13/819,743, dated Sep. 9, 2014.
Office Action issued by the U.S. Patent and Trademark Office, dated Apr. 27, 2017, for related U.S. Appl. No. 13/819,743; 9 pages.
Office Action issued by the U.S. Patent and Trademark Office, dated Jul. 7, 2017, for related U.S. Appl. No. 14/967,048; 11 pages.
Non-Final Office Action issued by the U.S. Patent and Trademark Office, dated Jan. 12, 2018, for related U.S. Appl. No. 13/819,743, 10 pages.
Non-Final Office Action issued by the U.S. Patent and Trademark Office, dated May 8, 2018, for related U.S. Appl. No. 14/967,048, 12 pages.
Non-Final Office Action issued by the U.S. Patent and Trademark Office, dated Sep. 21, 2017, for related U.S. Appl. No. 15/042,160, 9 pages.

* cited by examiner

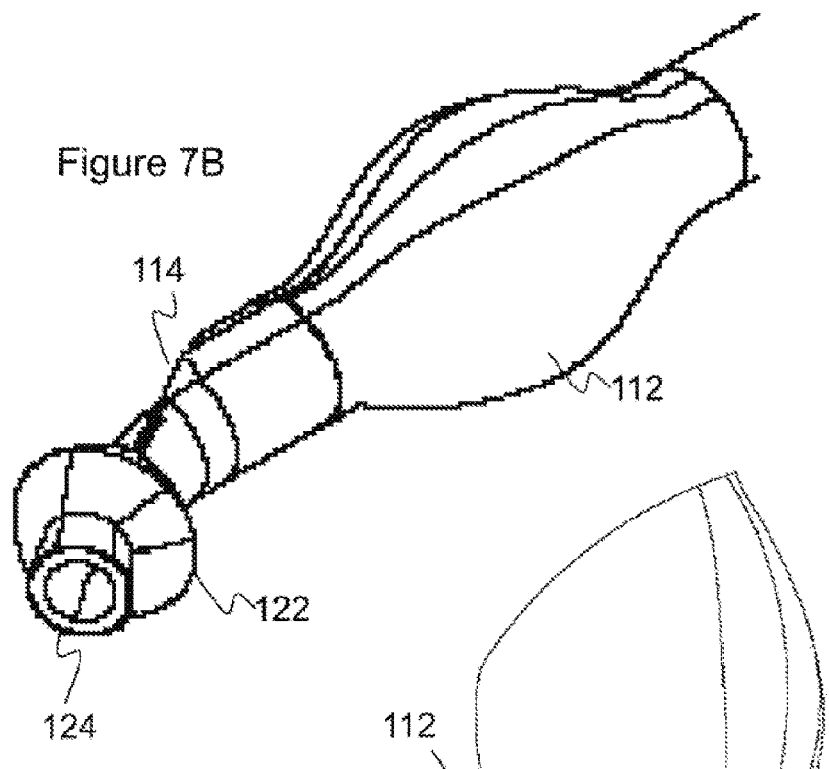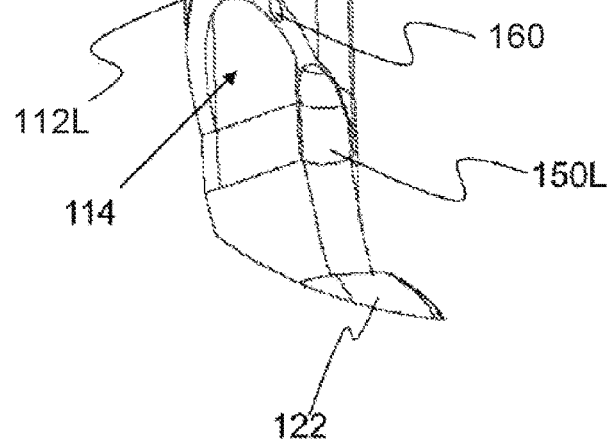

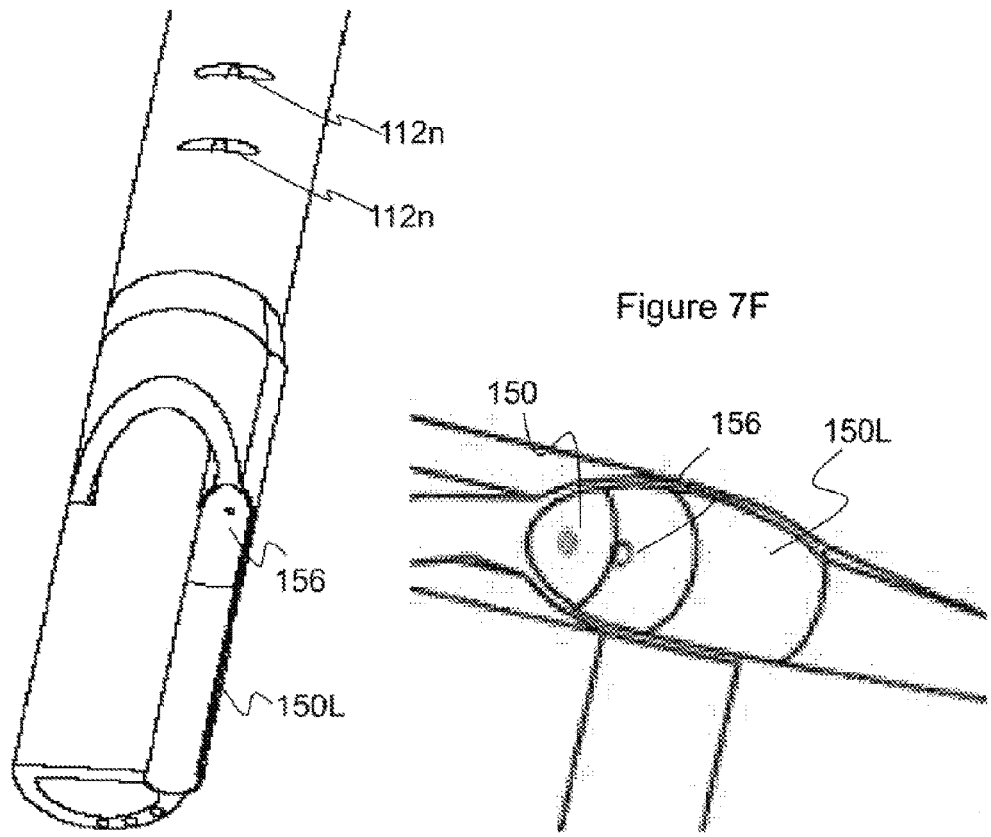
Figure 7D
Figure 7F
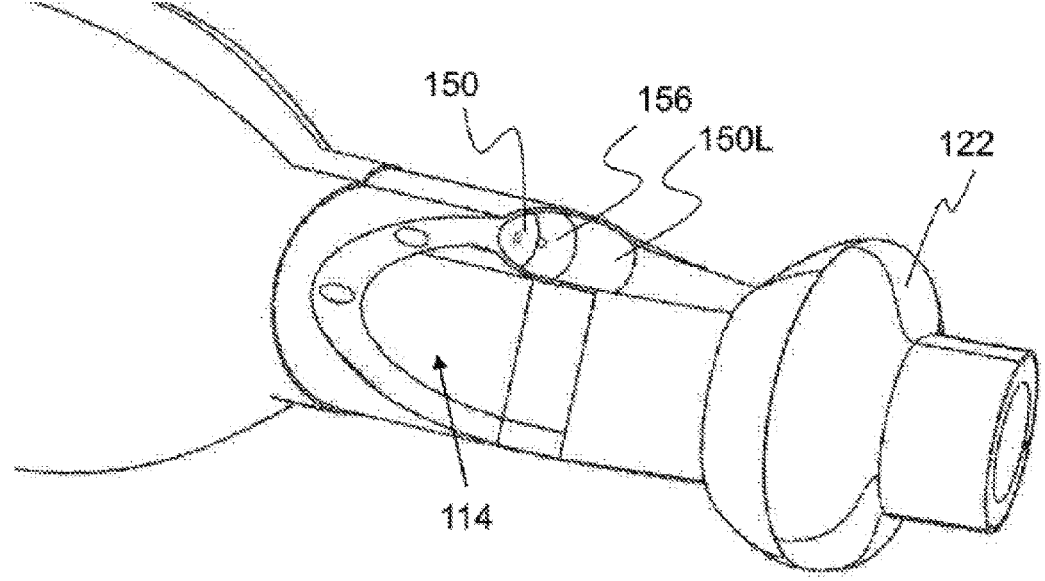
Figure 7E

ENDOBRONCHIAL TUBE WITH INTEGRATED IMAGE SENSOR AND A CLEANING NOZZLE ARRANGEMENT

CROSS-REFERENCE TO RELATED APPLICATIONS

This application is a U.S. Continuation In Part Application of International Application No. PCT/IB2012/052077, filed on Apr. 26, 2012, which claims the benefit of U.S. Provisional Application Ser. No. 61/506,210, filed on Jul. 11, 2011, all of which are hereby incorporated by reference in their entirety. U.S. application Ser. No. 14/151,846, filed on Jan. 10, 2014, which issued on Dec. 11, 2018 as U.S. Pat. No. 10,149,602, is a Continuation In Part of the present application. U.S. application Ser. No. 13/819,743, filed on Feb. 28, 2013, is a National Stage Entry of PCT/IB2012/052077. U.S. application Ser. No. 14/967,048, filed on Dec. 11, 2015, and Ser. No. 15/042,160, filed on Feb. 12, 2016, are continuations of U.S. application Ser. No. 13/819,743.

FIELD OF INVENTION

The present invention relates to upper airway tubes and in particular, to an endobronchial tube with an integrated image sensor and light source having a cleaning nozzle arrangement.

BACKGROUND OF THE INVENTION

Respiratory tubes for example endobronchial tubes, endotracheal tubes, tracheostomy tubes are used to ventilate at least a portion of the respiratory system or lungs of a subject. Such respiratory tubes may be inserted in a number of ways via a non-invasive approach through an orifice or cavity such as the oral or nasal cavity. Alternatively such tubes may be introduced to a body via a minimally invasive external incision creating a port for tube insertion for example through the trachea in a tracheotomy procedure.

Such respiratory tubes may be provided as double lumen tubes, or single lumen tubes for selectively ventilating a portion of the respiratory system. For example endobronchial tubes, whether, double lumen tubes or a single lumen tube may be utilized for one-lung ventilation procedures or for selective lung ventilation of the left or right bronchi, during one-lung ventilation procedures.

SUMMARY OF THE INVENTION

In order to perform one lung ventilation procedures without complications, the position of the respiratory tube placed within either the left or right bronchi and the trachea must be closely monitored or at least confirmed prior to initiating a procedure. Various technologies are available to confirm the tube's placement, for example capnograph, auscultation, bronchoscope and x-ray.

However these procedures take time, technique and skill to perform and therefore it is not feasible to continuously monitor the tube's placement.

In particularly when the subject is moved during a procedure the tube's location may change leading to potentially dangerous displacement of the tube possibly suffocating the subject or inappropriate ventilation of the patient, for example not ventilating the correct portion of the respiratory system.

Verification by means of a bronchoscope is currently the gold standard, but none of the mentioned confirmation techniques provide continuous monitoring of the carina or provide for correct tube positioning. Furthermore, drawbacks with respect to the design and sensitivity of the bronchoscope render its cleaning process elaborate and often inefficient and costly process, that may lead to cross infection between subjects.

There is an unmet need for, and it would be highly useful to have an endobronchial tube capable of continuously and seamlessly inspect the location and implantation of the endobronchial tube relative to the Tracheal Carina. Furthermore it would be advantageous to have an endobronchial tube that is capable of maintaining a clear field of view of the Tracheal Carina.

The present invention overcomes the deficiencies of the background by providing an endobronchial tube having an integrated image sensor with a corresponding light source and integrated means for maintaining the field of view provided by the image sensor, for example in the form of a cleaning nozzle and/or lumen.

A preferred embodiment of the present invention provides for a respiratory tube, preferably in the form of a double lumen endobronchial tube, designed for oral or nasal insertion via the trachea and into a lung to inspect and/or visualize the Carina, to maintain airway patency and/or deliver anesthetic, inhalation agent or other medical gases, and secure ventilation.

Most preferably the endobronchial tube of the present invention may be made of medical grade materials for example including but not limited to plastic, rubber, polymers or silicone or the like materials as is known in the art.

Most preferably the endobronchial tube of the present invention provides for continuous monitoring of the Tracheal Carina (herein "TC"), allowing a user, physician, nurse, or caregiver to verify the correct placement of the endobronchial tube while maintaining a clear field of view of the TC.

Most preferably the endobronchial tube includes an integrated image sensor, optionally and preferably in the form of a charged-coupled device ("CCD") or a complementary metal-oxide semiconductor ("CMOS") camera provided for visualizing the carina to confirm the correct placement of the tube within the trachea and bronchi, assuring correct ventilation during procedures for example including but not limited to one lung ventilation procedures, or the like.

Most preferably the integrated camera and light source provide continuous verification of the correct placement of the endobronchial tube. The continuous placement verification allows a caregiver the opportunity to detect any dangerous situation, for example cuff dislodgement, providing sufficient time to react to the situation as is necessary. Moreover blood and secretion accumulation or any other unexpected incidents during surgery, which might cause risk to the patient, may be observed.

A preferred embodiment of the present invention provides for an endobronchial tube with an integrated image sensor, for example including but not limited to a charged-coupled device ("CCD") or complementary metal-oxide semiconductor ("CMOS") camera, with a corresponding light source, for example including but not limited to a Light Emitting Diode ('LED') while optimizing the lumen patency for both adequate airflow performance through the tube. Most preferably the image sensor and corresponding light source are provided in a dedicated lumen along the length of the endobronchial tube. Most preferably the image sensor is further provided with at least one or more adjacent and integrated cleaning nozzle to ensure an open field of view, for example of the TC, distal to the image sensor. Most preferably the integrated cleaning nozzle may be configured to be wholly embedded within the tube's wall in the form of a dedicated cleaning lumen running the length of the tube. Most preferably the length of the image sensor lumen 150L is provided paralleled with the length of the tracheal lumen, therein both tracheal lumen and image sensor lumen are of essentially the same length. Optionally the length of the image sensor lumen 150L may be provided according to the length of the bronchial lumen.

Optionally the endobronchial tube may be provided with two dedicated image sensor lumen. Optionally a first dedicated image sensor lumen is provided according to the length of the tracheal lumen and a second dedicated image sensor lumen is provided according to the length of the bronchial lumen.

A preferred embodiment of the present invention provides for an endobronchial tube having an integrated image sensor, light source and cleaning nozzle capable of providing a continuously and unobstructed view and illumination of the carina, left bronchi, right bronchi, bronchial cuff and bronchial bifurcations, within a single field of view.

Optionally and preferably the tube of the present invention utilizes at least one or more bronchial cuff. Optionally at least two or more bronchial cuffs may be utilized to provide adequate sealing of the bronchi.

Optionally the bronchial cuff may be provided in varying shapes so as to better fit the bronchi for example include but is not limited to spherical, elliptical, helical, hourglass, trapezoidal, or the like.

Optionally different bronchial cuff configured and shaped according to anatomy and placement location, for example anatomy based on configuration of a cuff for left bronchi placement and for right bronchi placement. Within the context of this application the term endobronchial tube may be used interchangeably with any one of Tracheobronchial tube, double lumen tube, double lumen endobronchial tube, double lumen endotracheal tube, to collectively refer to a tube and/or catheter utilized for selectively ventilating a subject via both lungs, one of the lungs or a portion of one or both of the lungs.

An endobronchial tube comprising an external wall and an internal septum defining at least two ventilation lumen of different lengths for selectively associating with a patient about at least two locations relative to the Tracheal Carina, the tube comprising:

a first ventilation lumen having an open distal end that associates proximally to the Carina within the Trachea, with a first inflatable cuff; and a second ventilation lumen having an open distal end that extends distally, past the Carina and associates within one of the Left Bronchial branch or Right Bronchial branch with a second inflatable cuff;

the tube further comprising at least two peripheral lumen of different lengths, that are disposed within the tube's external wall and running parallel with the at least the first ventilation lumen;

the first peripheral lumen comprises an image sensor and light source disposed proximal to the distal end of the first ventilation lumen, and configured to provide an image of the Tracheal bifurcation of the Tracheal Carina, the openings of the Left Bronchial branch, and the opening Right Bronchial branch;

the second peripheral lumen defining a dedicated cleaning lumen, having a distal end disposed distally to the distal end of the first peripheral lumen about the image sensor and light source, the second peripheral lumen having a distal end having a plurality of variably sized openings, wherein each opening forms a cleaning nozzle distal to the image sensor, the second peripheral lumen configured to conduct a flowing fluid to maintain a clear field of view distal to the image sensor.

Optionally and preferably the distal end of the second peripheral lumen comprises four openings defining four cleaning nozzles about the image sensor. The four openings are preferably arranged distally to one another in a linear sequential manner. The first opening having an opening of about 0.8 mm defining the first cleaning nozzle directly adjacent to the image sensor. The remaining three openings may be configured to have a nozzle opening of about 0.6 mm.

Optionally the cleaning nozzles may be variably spaced relative to one another and/or may be uniformly spaced relative to one another about the distal end of the second peripheral lumen.

Optionally, the tube may further comprise additional peripheral lumen running along the second ventilation lumen providing for a second image sensor and light source providing an image of the Right bronchi or Left bronchi, and dedicated cleaning lumen.

Optionally the first and second peripheral lumen may run parallel with the second ventilation lumen rather than the first ventilation lumen.

Optionally the image sensor may be a CCD image sensor or CMOS Image sensor.

Optionally, the first peripheral lumen further comprises a light source disposed proximal to the distal end and adjacent to the image sensor.

Optionally the light source may be selected from the group consisting of a LED, optical fiber, waveguide, light guide, and any combination thereof.

Optionally the first peripheral lumen comprising an image sensor and light source may be disposed within a dedicated channel embedded within a wall of the first lumen.

Most preferably the image sensor may be associated with an auxiliary device for example including but not limited to a display and power supply at the proximal end of the tube most preferably about the first lumen, through a single dedicated connector for example including but not limited to a USB connector.

Optionally the endotracheal tube may be adapted for non-invasive insertion through the oral cavity or nasal cavity.

Optionally the endotracheal tube may be adapted for insertion through an external port or incision.

Optionally the endotracheal tube may be adapted for insertion through a surgical procedure or other invasive procedure.

Unless otherwise defined, all technical and scientific terms used herein have the same meaning as commonly understood by one of ordinary skill in the art to which this invention belongs. The materials, methods, and examples provided herein are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 1A shows the endobronchial tube within the right bronchi; FIG. 1B shows the endobronchial tube within the left bronchi;

FIGS. 7A-F shows varying close up views of the distal end of the endobronchial tube according to optional embodiments of the present invention;

DESCRIPTION OF THE PREFERRED EMBODIMENTS

The principles and operation of the present invention may be better understood with reference to the drawings and the accompanying description. The following reference labels listed below are used throughout the drawings to refer to objects having similar function, meaning, role, or objective.

10 Stylet;
12 Y-connector;
14 Air Balance Cap;
20 Endobronchial Tube connector assembly;
22 Endobronchial Tube connector proximal end;
24 Tracheal lumen connector portion;
26 Bronchial lumen connector portion;
28 Endobronchial Tube connector distal end;
50 endobronchial tube system;
100 endobronchial tube;
100w tube external wall;
101 sectional view;
102 tube proximal end;
104 tube distal end;
104a distal curvature;
106 tube medial portion;
106a medial curvature;
108 midline partition;
110 tracheal lumen;
111 tracheal lumen connector;
112 tracheal cuff;
112n tracheal cuff notch;
114 tracheal lumen distal end;
116 tracheal lumen proximal end;
118 tracheal cuff connector;
120 bronchial lumen;
122 bronchial cuff;
124 bronchial lumen distal end;
126 bronchial lumen proximal end;
128 bronchial cuff connector;
130 injection tube connector;
150 image sensor arrangement;
150c image sensor;
150d image sensor lumen distal end;
150I illumination source;
150L image sensor lumen;
152 image sensor notch;
154 image sensor conductor;
156 image sensor single cleaning nozzle;
158 image sensor connector;
160 cleaning lumen;
160d cleaning lumen distal end;
162 cleaning nozzle arrangement;
164 four cleaning nozzle arrangement;
166 primary cleaning nozzle;
168 secondary cleaning nozzles;
TR Trachea;
TC Tracheal Carina; BR Right Bronchi;
BL Left Bronchi.

Figure 1A:
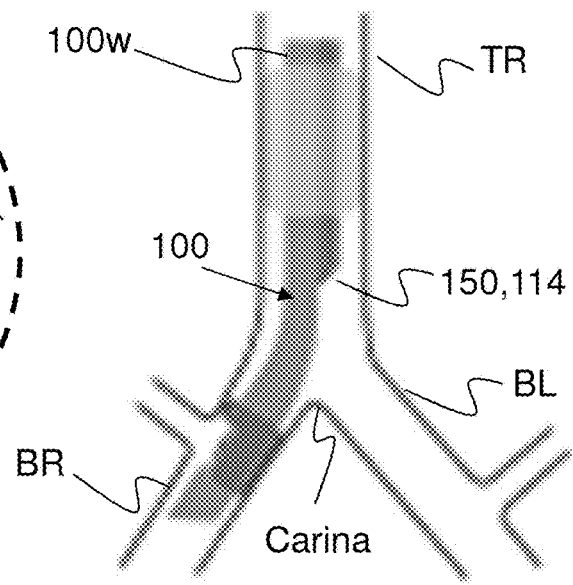
FIGS. 1A-B show schematic illustrations of an exemplary endobronchial tube according to an optional embodiment of the present invention.
Figure 1B:
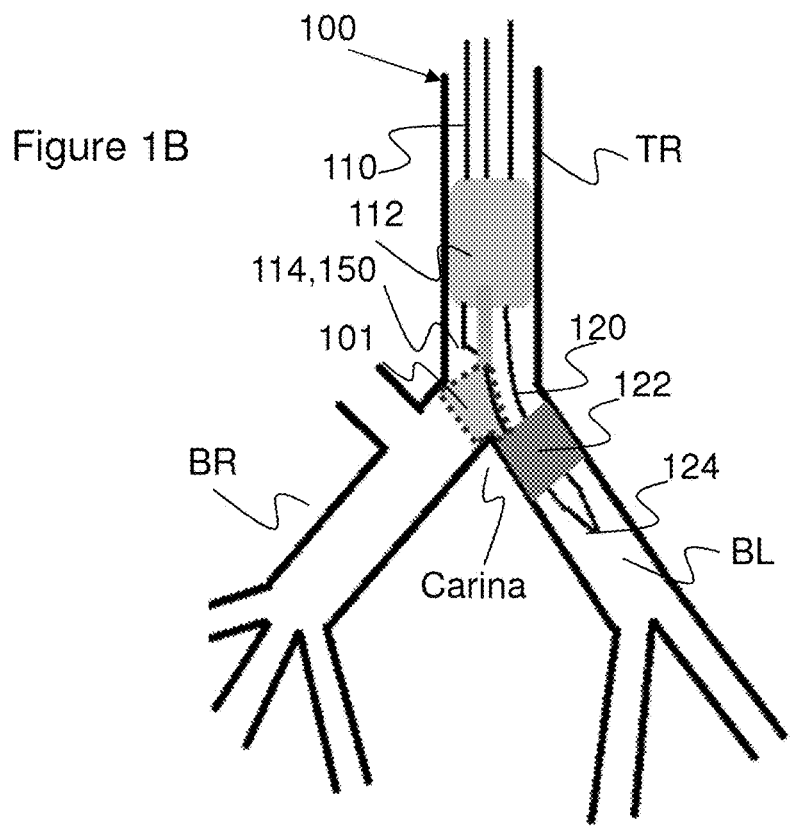

FIG. 1A shows a schematic illustration of an exemplary endobronchial tube 100 according to an optional embodiment of the present invention placed within the right bronchi (BR). FIG. 1B shows a schematic illustration of an endobronchial tube 100 within the left bronchi(BL).

Endobronchial tube 100 is a dual lumen tube comprising an external wall 100w, a first tracheal ventilation lumen 110 and a second bronchial ventilation lumen 120. Most preferably wall 100w is a common to both tracheal lumen 110 and bronchial lumen 120 wherein wall 100w most preferably defines the external surface of tube 100. Most preferably an internal septum and/or midline partition 108 defines the individual lumen into tracheal lumen 110 and bronchial lumen 120, FIGS. 8A-B. Tracheal lumen 110, most preferably, has a distal end 114 ending within the trachea while the bronchial lumen 120 has a distal end 124 endings within the bronchi, left or right. Therein tracheal lumen 110 and bronchial lumen 120 are configured to have different lengths, wherein the bronchial lumen 120 extends past and/or distally to tracheal lumen 110.

Most preferably each ventilation lumen comprising an inflatable cuff respectfully, tracheal cuff 112 and bronchial cuff 122. Optionally and preferably cuffs 112 and 122 are individually controllable. Tube 100 is places such that the tracheal lumen 110 is placed within the Trachea by way of cuff 112 proximally, above, the tracheal carina ('TC'). Most preferably the tracheal carina may be continually visualized with an image sensor 150c and light source 150L, FIG. 9.

Figure 8A:
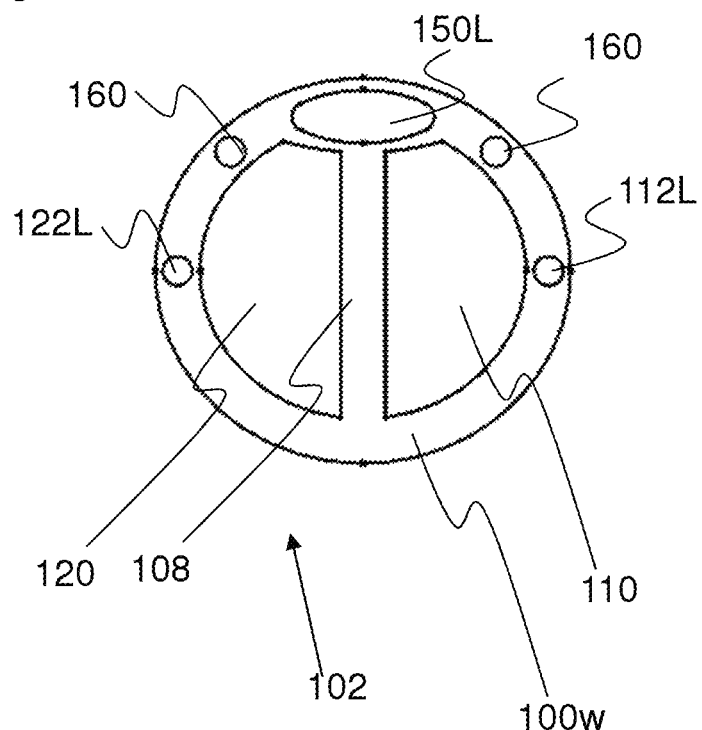
FIGS. 8A-B show cross-sectional views about different portions of the endobronchial tube according to optional embodiments of the present invention.
Figure 8B:
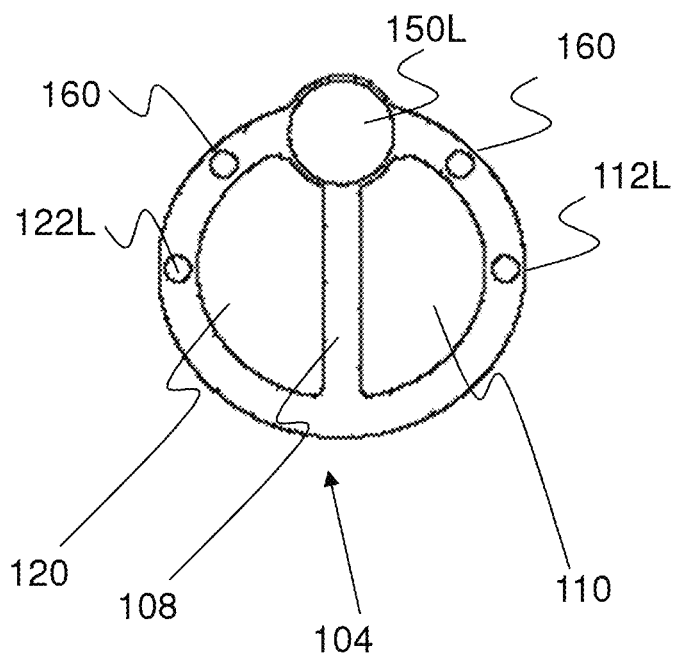

Most preferably wall 100w of tube 100 comprises a plurality of dedicated peripheral lumen dispersed about the periphery of wall 100w, FIGS. 8A-B. Most preferably tube 100 comprises at least two or more dedicated peripheral lumen; a first dedicated peripheral lumen provided as an image sensor lumen 150L provided for imaging the TC; and a second dedicated peripheral lumen provided in the form of a dedicated cleaning lumen 160 for clearing and/or cleaning the view of image sensor disposed in image sensor lumen 150L.

Figure 2:
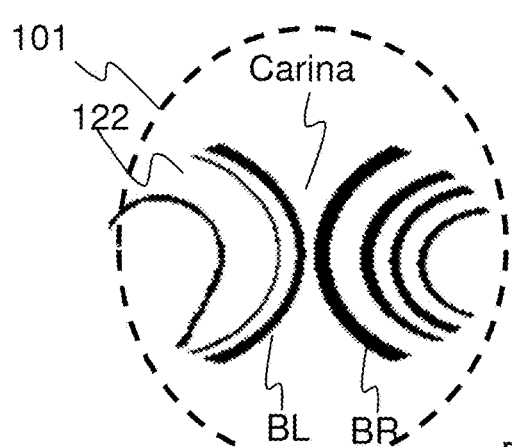
FIG. 2 shows a schematic sectional view of the Tracheal Carina as seen from the endobronchial tube according to an optional embodiment of the present invention.
Figure 7A:
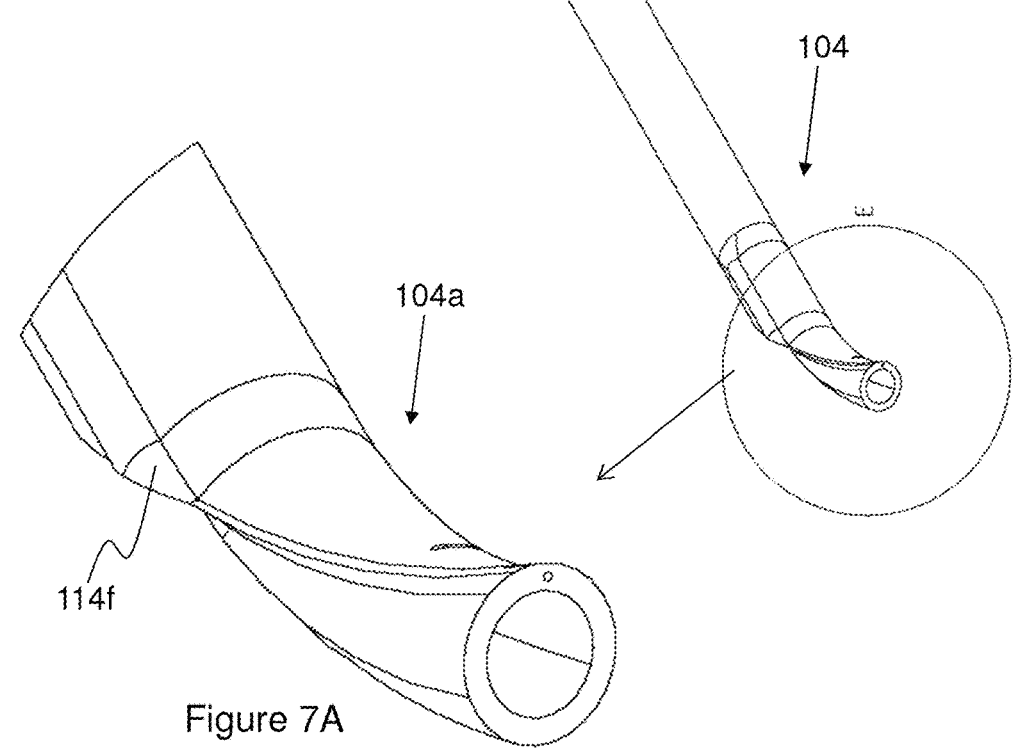
Figure 7G:
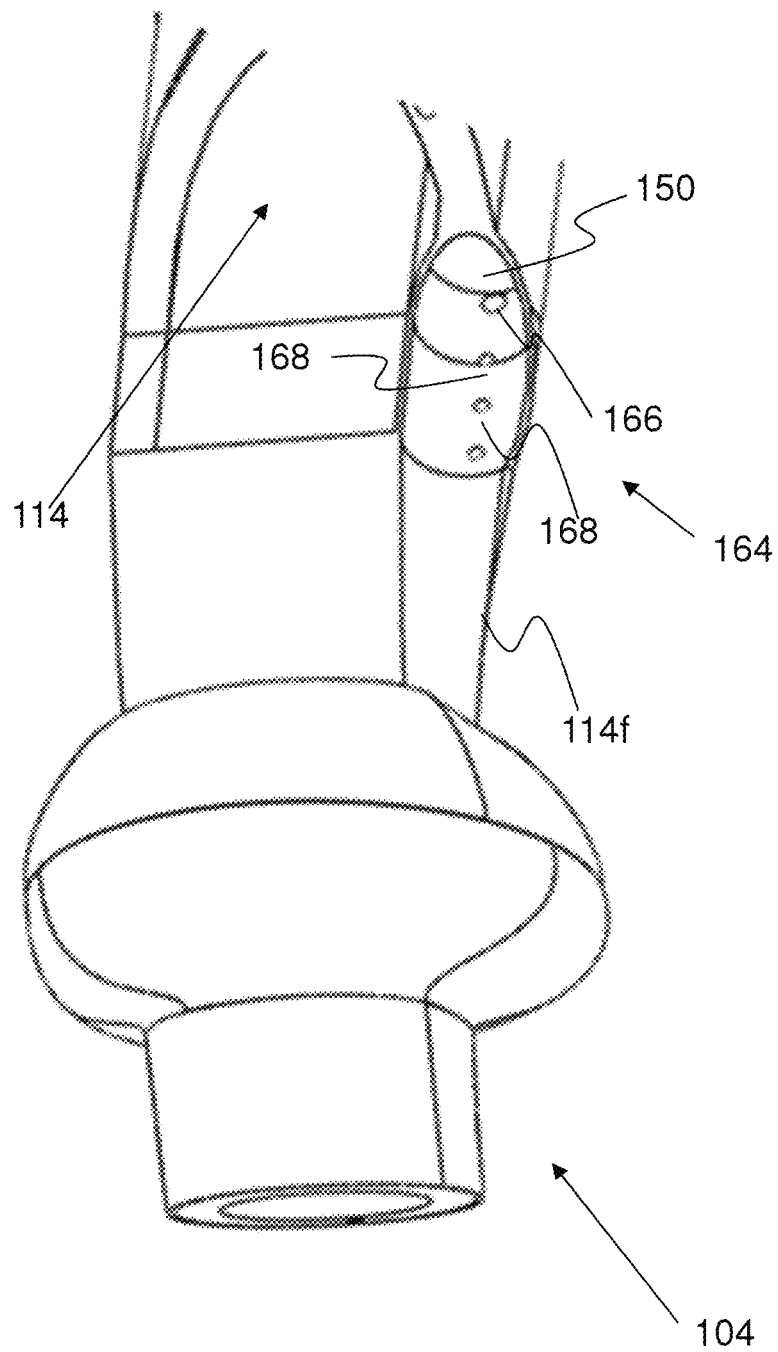
FIGS. 7G-H show a preferred embodiment of the cleaning nozzle arrangement according to the present invention.
Figure 7H:
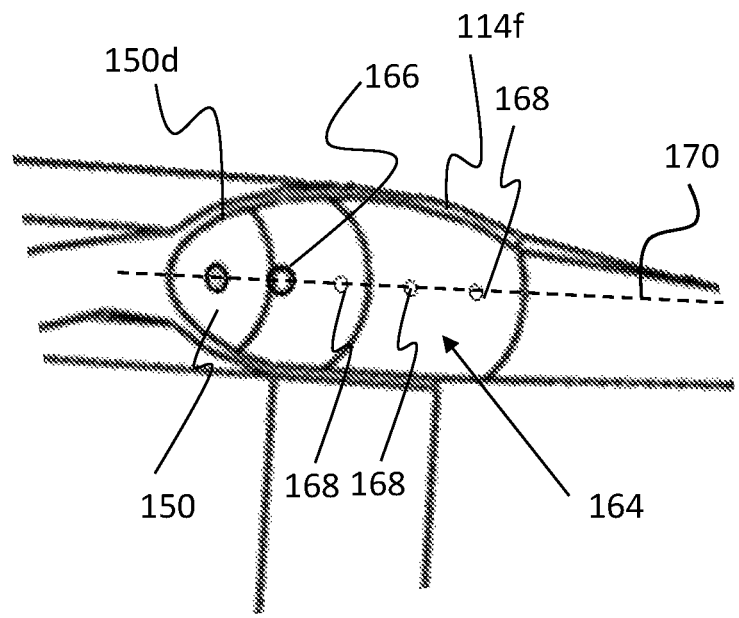

Most preferably tube 100 according to the present invention is characterized in that it comprises a cleaning nozzle arrangement 162 about distal end 160d, FIGS. 7G-H. Most preferably cleaning nozzle arrangement 162 comprises a plurality of cleaning nozzles arranged about the distal end 160d and distally to image sensor arrangement 150 so as to ensure that a tube 100 is provided with a clear and unobstructed view of the TC, for example as shown in FIG. 2. Most preferably cleaning nozzle arrangement are optionally and preferably directed and/or aimed to clear the field of view immediately distal to image sensor arrangement 150 about the distal end 114 of tracheal ventilation lumen 110.

Optionally and most preferably cleaning nozzle arrangement 162 may comprise at least two or more cleaning nozzles about distal end 160d. Most preferably a cleaning nozzle arrangement 162 comprising a plurality of cleaning nozzles about distal end 160d provides sufficient flushing and/or cleaning power and/or force and/or pressure so as to provide image sensor arrangement 150 with an unobstructed view by evacuating biological debris for example mucus or the like biological builds up in and about distal end 114, 150d and 160d.

Most preferably cleaning nozzle arrangement 162 comprises a four cleaning nozzle arrangement 164 about image sensor arrangement 150. Four cleaning nozzle arrangement 164 includes a first primary cleaning nozzle 166 and at least three secondary cleaning nozzles collectively referred to as 168, as shown in FIGS. 7G-H.

Most preferably arrangement 164 may be arranged distally to one another in a linear sequential manner for example as shown in FIG. 7G-H. Most preferably primary cleaning nozzle 166 may be configured to have a nozzle opening of about 0.8 mm, and is most preferably disposed immediately and/or directly adjacent to the image sensor arrangement 150.

Most preferably secondary cleaning nozzles 168 may be configured to have a nozzle opening of about 0.6 mm, and a disposed distally to primary cleaning nozzle 166.

Optionally secondary cleaning nozzles 168 may optionally be spaced apart equally, for example about 0.5 mm. Optionally secondary cleaning nozzles 168 may be spaced unequally distal to primary cleaning nozzle 164.

Figure 7I:
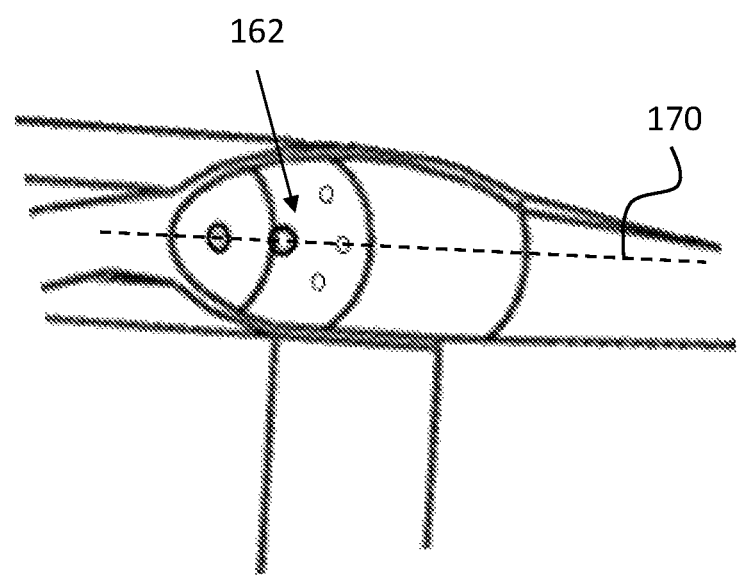
FIG. 7I shows an optional embodiment according to the present invention.

Optionally cleaning nozzle arrangement 162 about distal end 160d may be configured in optional geometric arrangements, wherein primary cleaning nozzle 166 is disposed nearest to image sensor arrangement 150 providing a first flushing and/or cleaning activity, while a plurality of secondary cleaning nozzle 168 are arranged distally thereto to provide a secondary flushing and/or cleaning activity, FIG. 7I.

Optionally cleaning nozzles 166, 168 may be provided with an opening having a diameter from about 0.1 mm to about 2 mm. Optionally primary cleaning nozzle 166 has a larger nozzle opening diameter than do secondary cleaning nozzles 168.

Most preferably image sensor 150c and light source 150l are disposed within a first dedicated peripheral image sensor lumen 150L that is most preferably disposed within wall 110w. Optionally and most preferably image sensor lumen 150L comprising image sensor 150c and light source 150l may be integrated within tracheal lumen 110 about distal end 114, such that the distal end 150d is adjacent to distal end 114. Optionally and most preferably the image sensor arrangement 150 remains within its dedicated peripheral image sensor lumen 150L. Optionally and most preferably image sensor arrangement 150, FIG. 9, comprising an image sensor 150c and a light source 150l may be integrated within a dedicated channel or peripheral image sensor lumen 150L within a wall of the tracheal lumen 110. Most preferably image sensor arrangement 150 provides a cross sectional view 101, for example as shown in FIG. 2.

Most preferably image sensor arrangement 150 are provided in the form of at least one or more light emitting diode ('LED') 150l and image sensor 150c for example including but not limited to a charged-coupled device ("CCD") or a complementary metal-oxide semiconductor ("CMOS"), (FIG. 9) providing a view 101 showing the status of the bronchi, FIG. 2.

FIG. 2 shows a schematic sectional view of the Tracheal Carina as seen from endobronchial tube 100, provided by image sensor and light source 150, allowing the visualization of bronchial cuff 122 disposed within the left bronchi BL, the patency of the left bronchi, the patency of the right bronchi, the tracheal carina, bronchial bifurcation, in a single field of view 101. Optionally a similar view may be provided with image sensor arrangement 150 when tube 100 is disposed with the right Bronchi BR as shown in FIG. 1A.

Figure 3:
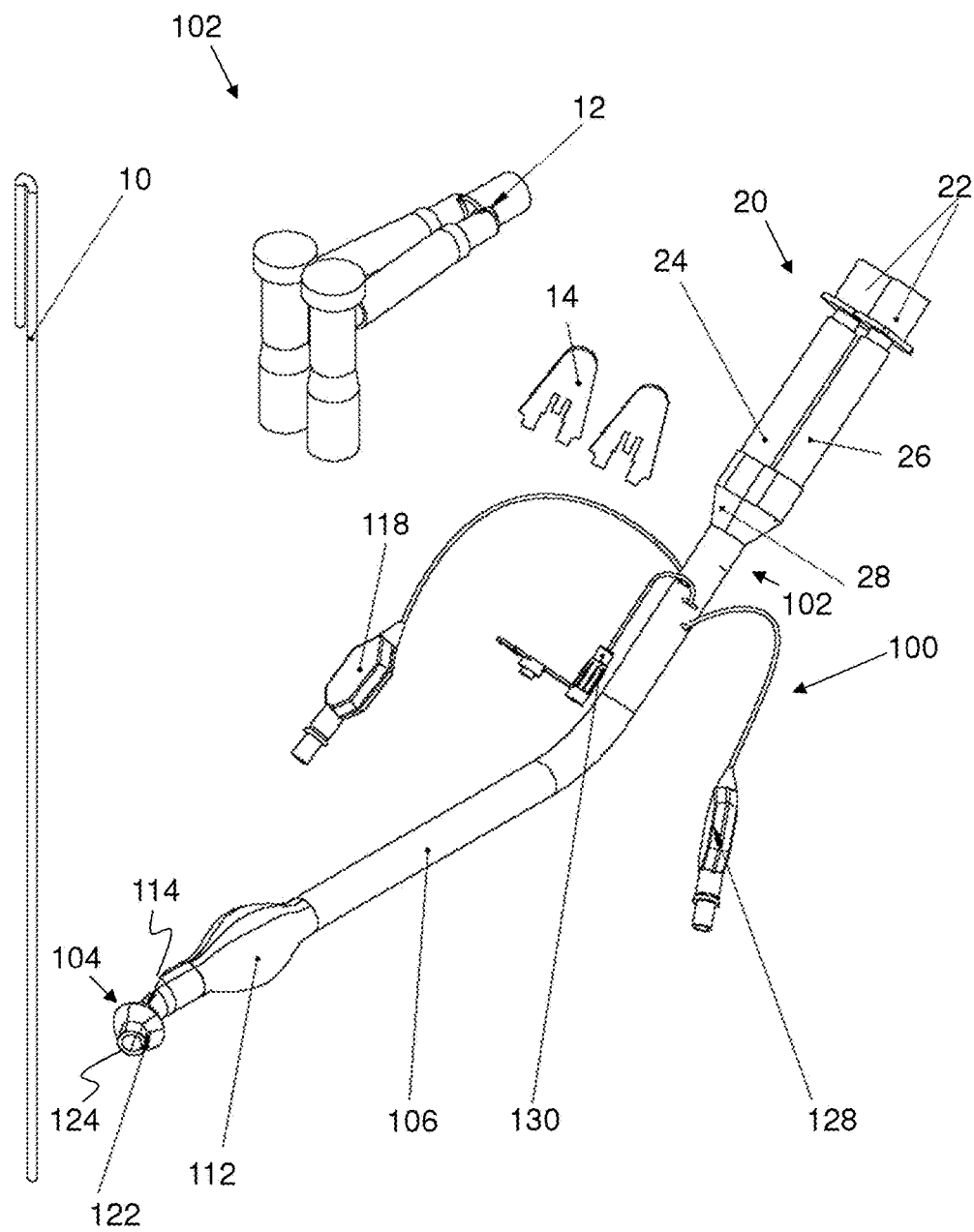
FIG. 3 shows a perspective view of an exemplary endobronchial tube according to an optional embodiment of the present invention.

FIG. 3 shows endobronchial double lumen tube system 50 comprising endobronchial tube 100 and optional various auxiliary devices that may be used in conjunction with and/or facilitate the use of tube 100.

Optionally auxiliary devices may for example include but are not limited to stylet 10, Y-connector 12, air balance caps 14, and an endobronchial tube connector assembly 20, or the like adjunct device utilized facilitating the use of tube 100 as is known in the art.

Stylet 10 most preferably is utilized to facilitate placement of tube 100, as is known and accepted in the art.

Y-connector 12 most preferably provides for simultaneously connecting both lumens of double lumen tube 100 to a single ventilation source.

Endobronchial Tube connector assembly 20 provides for individually connecting to tracheal lumen 110 and bronchial lumen 120. Connector assembly 20 comprises a proximal end 22, distal end 28, and respective Tracheal lumen connector portion 24 and Bronchial connector portion 26.

Most preferably proximal end 22 provides for connecting and/or otherwise associating the tube 100 at proximal end 102 at about the individual lumen tracheal lumen 110 and bronchial lumen 120 to auxiliary devices for example including but not limited to ventilation sources.

Most preferably distal end 24 provides for coupling and/or otherwise associating with tube 100.

FIG. 3 further provides a perspective view of a preferred double lumen endobronchial tube 100 comprising tracheal lumen 110 having a tracheal lumen distal end 114 and bronchial lumen 120 having a bronchial lumen distal end 124.

Tube 100 further comprises tracheal cuff 112, shown in its expanded state, provided for securely placing and/or anchoring tube 100 within the trachea while ventilating the lungs through tracheal lumen 110.

Tube 100 further comprises bronchial cuff 122, shown in its expanded and/or inflated state, provided for securely placing and/or anchoring tube 100 within the bronchi, left or right. Most preferably cuff 122 provides for selectively controlling the ventilation to the bronchial arch wherein it is placed (left or right). For example ventilation to either the left or right bronchi may be completely blocked so as to allow a procedure on the respective lung (for example right) while allowing the ventilation of the other lung (for example left) via tracheal lumen 110.

Most preferably tracheal cuff 112 may be inflated and/or deflated via cuff tracheal connector 118.

Most preferably bronchial cuff 122 may be inflated and/or deflated via cuff bronchial connector 128.

Most preferably injection tube connector 130 provides an access point to a dedicated lumen about each of the tracheal tube 110 and bronchial tube 120, preferably for delivering drugs, suctioning liquids about tracheal distal 114 and/or bronchial lumen distal end 124.

Figures 4A, 4B:
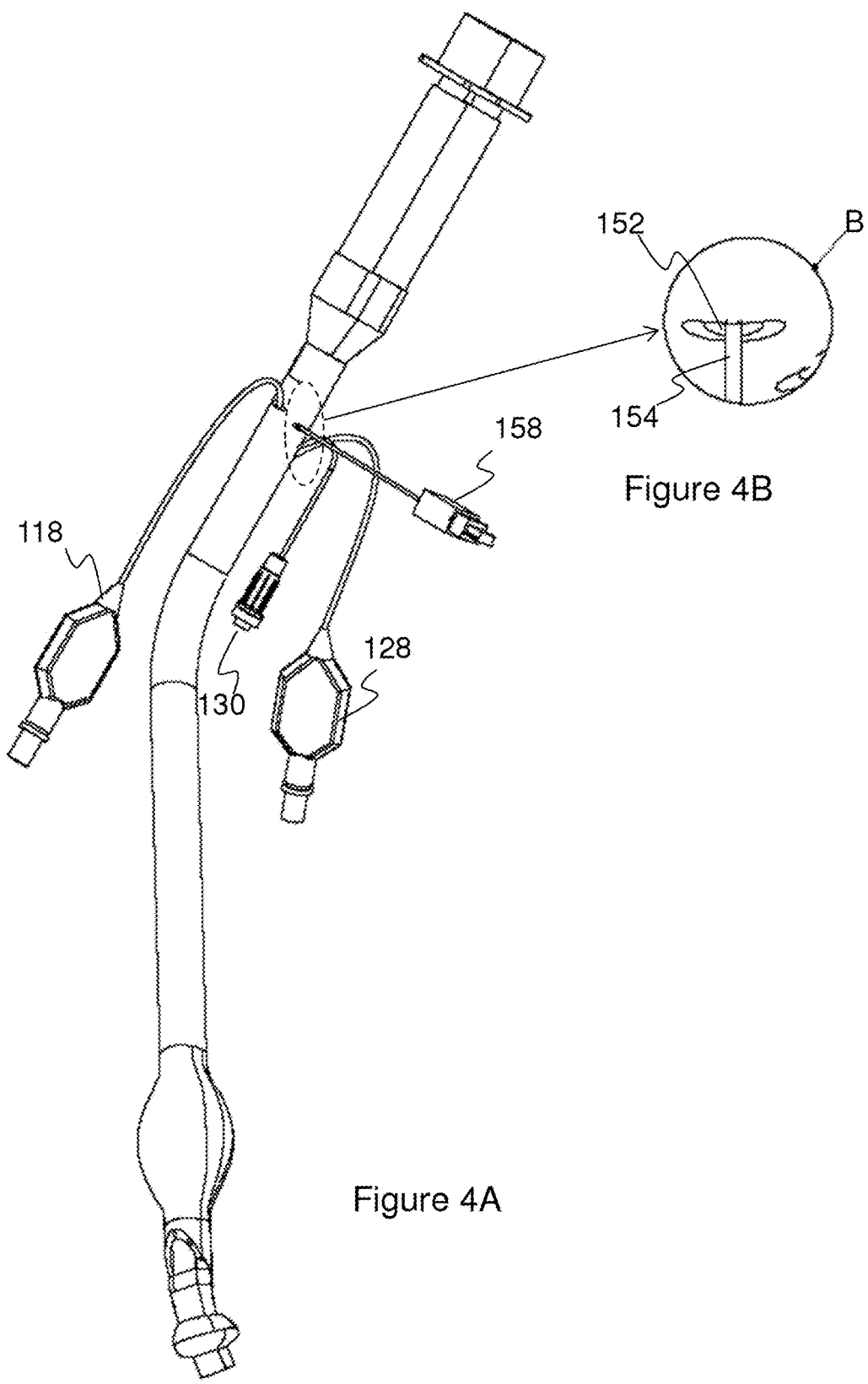
FIG. 4A shows a perspective view of an exemplary endobronchial tube according to an optional embodiment of the present invention.
FIG. 4B shows a close up view of notch exit point for the image sensor connector according to the present invention.

FIG. 4A provides a further perspective view of endobronchial tube 100, showing image sensor connector 158. Most preferably image sensor connector 158 is provided in the form of a USB connector that provides both for image and power supply to image sensor arrangement 150 disposed in a dedicated lumen near distal end 114. Optionally and preferably image sensor 150c and illumination source 150l may be rendered functional when connected to a display and power source (not shown) via connector 158.

FIG. 4B provides a close up view showing the image sensor notch 152 disposed about the proximal end of image sensor lumen 150L providing an exit point for image sensor image sensor conductors 154, most preferably provided for both image transfer and power supply to image sensor 150c and illumination source 150I.

Figure 5:
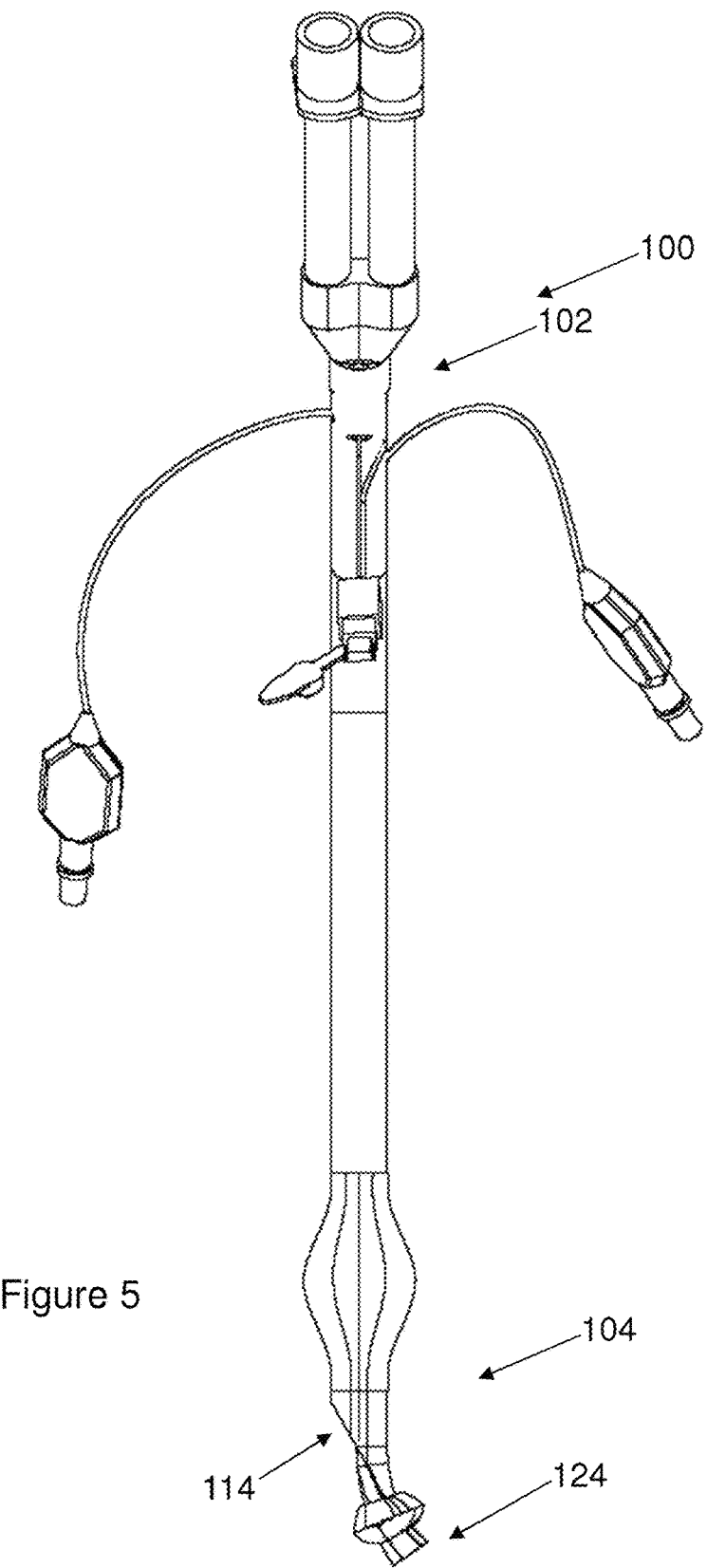
FIG. 5 shows a perspective view of exemplary endobronchial tube according to an optional embodiment of the present invention.

FIG. 5 provides a further perspective view of tube 100 provided from a face on view showing the separation of tracheal lumen 110 and bronchial lumen 120 at distal end 104 of tube 100.

Figure 6:
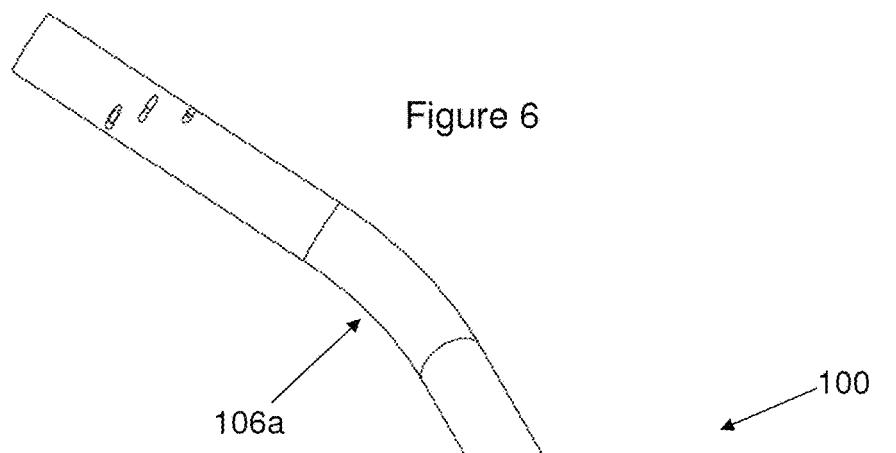
FIG. 6 shows a perspective view of exemplary endobronchial tube according to an optional embodiment of the present invention, depicting the curvature of the tube.

FIG. 6 provides a further schematic illustrative depiction of tube 100 showing a perspective view of tube 100 with the bronchial cuff 122 and tracheal cuff 112 removed. FIG. 6A shows the curvature provided at both the medial section 106 and distal end 104 therein defining a medial curvature 106a and a distal curvature 104a. Curvatures 104a and 106a are provided to so that tube 100 fits within the upper airway tract's anatomy.

Most preferably medial curvature 106a is provided for the ease of accessing and introducing tube 100 within the trachea through the oral cavity and pharynx. Most preferably, curvature 106a, is provided with an angle from about 100 degrees to about 160 degrees.

Most preferably distal curvature 104a is provides for ease of accessing and introducing distal end 104 into one of the bronchi, left or right.

Optionally and preferably distal curvature 104a may be specific for individual left or right endobronchial tubes. Optionally distal curvature may be configured to be from about 25 degrees to about 70 degrees. Optionally and preferably about 35 degrees as shown.

Optionally the length of tube 100 may be provided with a length from about 200 mm to about 550 mm. Optionally and preferably the length of tube 100 may be selected in accordance with a user's anatomy.

Optionally endobronchial tube 100 may be provided with different sizes, length, diameters as known and accepted in the art. Optionally tube 100 may be provided with a gauge from about 26 Fr to about 44 Fr, or from about For example the external diameter of tube 100 may be provided in varying gauges and/or sizes for example including but not limited to 28 Fr, 32 Fr, 35 Fr, 37 Fr, 39 Fr and 41 Fr, within the context of this application the units 'Fr' refer to the gauge of the tube 100 in the units French as is a common term of the art. Alternatively the gauge and or size of tube 100 may be provided in the SI units of millimeters 'mm'. The tube 100 according to the present invention may be provided with an external diameter of about 9.3 mm, 10.7 mm, 11.7 mm, 13 mm and 13.7 mm.

Optionally and preferably the length and diameter (also referred to as gauge) of tube 100 may be correlated with one another.

FIG. 7A shows a close up view of distal end 104 of tube 100 shown in FIG. 6 providing a close up view. FIG. 7A further shows a close up view of curvature 104a showing the flaring 114f of distal end 104 from wall 100w of tracheal lumen into the side portion of bronchial lumen 120, most preferably forming a distal end flaring 114f. Most preferably flaring 114f at distal end 104 further provides for placing and/or approximating the distal ends 150d, 160d of the peripheral image sensor lumen 150L, 160 near the distal end 114 of ventilation lumen 110, for example as shown in FIG. 7C.

Most preferably flaring 114f forms a cover and/or cap over the distal end of the dedicated peripheral lumen 150d and 160d adjacent to distal end 114 of ventilation lumen 110.

Most preferably distal end flaring 114f facilitates placement of a cleaning nozzle arrangement 162 about the distal end 160d of cleaning lumen 160, for example as shown in FIGS. 7C and 7G. Optionally flaring 114f may facilitate the cleaning function provided by arrangement 162.

FIGS. 7A-E show various close up view of distal end 104 specific to curvature 104a showing the flaring 114f and tapering of distal end 104 from the tracheal lumen 110 into the side portion of bronchial lumen 120.

FIGS. 7D-E provide additional close up views of the distal end 150d and cleaning lumen 160 showing revealing an optional primary cleaning nozzle 166 in the form of a single cleaning nozzle 156, most preferably provided for cleaning image sensor 150c.

Optionally cleaning nozzle 156 may be provided with an opening having a diameter from about 0.1 mm to about 2 mm, more preferably from about 0.4 mm to about 0.9 mm, optionally about 0.6 mm or 0.8 mm.

Image sensor arrangement 150 is most preferably provided in image sensor lumen 150L that spans the length of tube 100. Most preferably image sensor lumen 150L is disposed between tracheal lumen 110 and bronchial lumen 120.

Most preferably distal end of image sensor lumen 150L provides for visualizing the carina and the bronchial cuff 122, for example as shown in FIG. 2.

Most preferably the diameter of image sensor lumen 150L is variable along the length of tube 100. Most preferably image sensor lumen 150L is smallest at the proximal end 102 and largest at the distal end 104. Optionally and preferably at proximal end 102 image sensor lumen 150L is configured to have an elliptical cross-section. Optionally and preferably at distal end of image sensor lumen 150L is configured to have a circular cross-section.

Most preferably alongside image sensor lumen 150L is a dedicated cleaning lumen 160 that has a distal end defining a cleaning nozzle 156, as shown, providing for cleaning image sensor 150c about its distal end.

Figure 10:
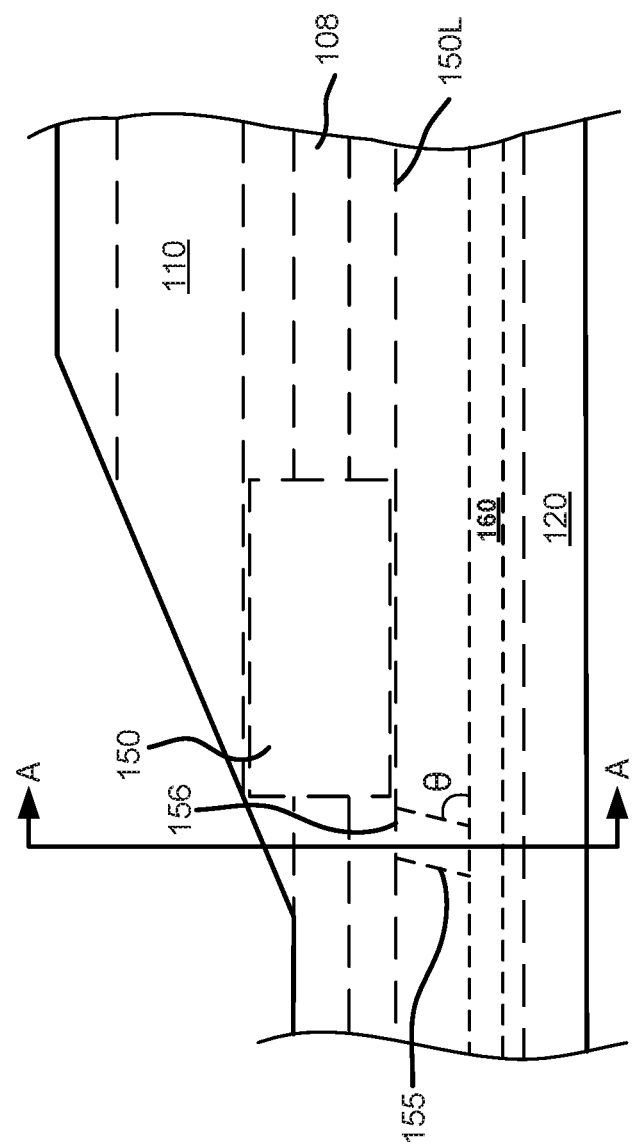
FIG. 10 illustrates a side view of a section of the endobronchial tube.

Optionally and preferably cleaning nozzle 156 is provided with a curvature and/or angle θ forming angled portion 155 (shown in FIG. 10) so as to direct cleaning solution, fluid, gas or the like flowing fluid toward and/or away from image sensor arrangement 150 and more preferably image sensor 150c. For example cleaning lumen 160 may be utilized to clear mucus or the like biological obstruction from in front of integrated image sensor arrangement 150 by flushing with a flowing fluid, for example a liquid or gas, from the proximal end of lumen 160 through to its distal end 160*d* and forming at least one or more cleaning nozzle 156, 166, 168 or a cleaning nozzle arrangement 162, 164. Optionally cleaning lumen 160 may be used to clear the viewing field of image sensor arrangement 150 by applying suctioning therein suctioning in front of the field of view to keep it clean.

FIG. 7F shows a close up view of cleaning nozzle 156 that is directed toward image sensor 150*c* about the distal end of image sensor lumen 150L. Optionally and preferably cleaning nozzle 156 is configured such that it provides for maintaining an open field of view of the Tracheal Carina for integrated images sensor 150*c*.

While FIG. 7E-F show an optional cleaning nozzle arrangement having a single cleaning nozzle 156, about the tube distal end 104, FIGS. 7G-H show a preferred embodiment of the present invention for a ventilation tube 100 having a four cleaning nozzle arrangement 164 comprising a plurality of cleaning nozzles, including a primary cleaning nozzle 166 and three secondary cleaning nozzle 168. FIG. 7G shows an illustrative diagram of the preferred embodiment showing cleaning nozzle arrangement 162 about the distal end 114. Most preferably nozzle arrangement 162 comprises a primary nozzle 166 and a plurality of secondary nozzles 168, as previously described. As shown a preferred embodiment comprises three secondary nozzles 168 disposed distally to primary nozzle 166 and image sensor 150*c*. Most preferably the cleaning nozzles comprising nozzle arrangement 162 are directed so as to clean and/or clear and/or suction any biological debris for example mucus that forms distally to image sensor 150. Plane 170 is a plane of a horizontal cross section of tube 100 wherein the image sensor 150, primary nozzle 166 and secondary nozzles 168 are located in the identical plane 170. In the embodiment of FIG. 7I, the image sensor 150, primary nozzle 166 and at least one of secondary nozzles 162 are located in the identical plane 170.

Optionally cleaning nozzles 166, 168 may be provided with an opening having a diameter from about 0.1 mm to about 2 mm. Optionally primary cleaning nozzle 166 has a larger nozzle opening diameter than do secondary cleaning nozzles 168.

FIG. 7H provides a close up view of four cleaning nozzle arrangement 164 about distal end 114, as previously described and according to a preferred embodiment of the present invention, wherein the nozzle arrangement is characterized by a distally linear arrangement wherein primary nozzle 166 is adjacent to image sensor 150*c* while secondary nozzles 168 are positioned distally therefrom, optionally and preferably at equidistant from one another.

FIG. 7I shows an optional cleaning nozzle arrangement 162 where a plurality of secondary cleaning nozzles 168 are arranged about image sensor 150*c* in a circumferential arrangement, for example as shown.

Optionally and preferably the distal end 160*d* of cleaning lumen 160 may be curved such that the distal end 160*d* and nozzle arrangements 162, 164 are most preferably directed toward the distal end 150*d* of image sensor lumen 150L therein providing for forming a cleaning nozzle arrangement 162 that is optionally and preferably directed toward image sensor 150*c*, for example as shown in FIG. 7E.

Optionally tube 100 may be provided with at least two or more peripheral cleaning lumen 160 for example as shown in FIGS. 8A-B. Optionally a first cleaning lumen may be provided for flushing biological obstruction while a second cleaning lumen may be provided for suctioning biological obstructions away from the distal end 114. Optionally a plurality of cleaning lumen 160 may be disposed on opposite sides of image sensor arrangement 150.

Optionally a plurality of cleaning lumen 160 may be configured to cooperate with one another, for example a first lumen would flush biological obstructions toward a second cleaning lumen where the obstruction is carried away by suctioning.

Optionally at least two or more cleaning lumen 160 may be utilized concertedly to either suction or flush obstructions distal to image sensors arrangement 150, therein most preferably ensuring an open viewing field.

Optionally a plurality of cleaning lumen may be provided with different diameters and or sizes.

FIG. 8A shows a cross sectional view of tube 100 about its proximal end 102 having tracheal lumen 110 and a bronchial lumen 120 defined on either side of a midline partition 108. Most preferably tube 100 comprises a plurality of peripheral lumen disposed internally and/or within the walls of tube 100. Most preferably a plurality of peripheral lumen may be disposed about the circumference of tube 100, within wall 100*w*, and span essentially the length of tube 100, about the tracheal lumen 110 and/or bronchial lumen 120. Optionally and preferably the peripheral lumen may for example include but is not limited to a suctioning lumen, cuff inflating lumen, electronic lumen, image sensor lumen, cleaning lumen, injection tube lumen, or the like.

Most preferably tube 100 includes an image sensor lumen 150L provided for image sensor 150*c* and integrated illumination source 150I. Most preferably image sensor lumen 150L provides for housing the image sensor 150 at its distal end (FIGS. 7E-F) and housing image sensor conductors, for example in the form of an image sensor conductor 154, disposed along the length of image sensor lumen 150L, and an image sensor notch 152 disposed near the proximal end of image sensor lumen 150L allowing image sensor conductor 154 and connector 158 to be disposed external to tube 100.

Optionally and preferably image sensor lumen 150L is disposed about the anterior portion of tube 100 about the middle of the cross-section of tube 100. Most preferably image sensor lumen 150L is disposed anterior to partition 108. Optionally image sensor lumen 150L may be disposed about the posterior portion of tube 100 therein posterior to partition 108.

Most preferably on both sides of image sensor lumen 150L are dedicated lumen running along the length of tube 100 and most preferably running parallel with image sensor lumen 150L. Optionally and preferably at least one or more of lumen are provided as a dedicated cleaning lumen 160. Optionally both lumen flanking image sensor lumen 150L may be dedicated cleaning lumen 160.

Most preferably tube wall further comprises lumen 112L and 122L respectively corresponding to tracheal lumen 110 and bronchial lumen 120. Optionally and preferably lumen 112L and 122L are provided for inflating and/or deflating cuffs 112 and 122 respectively.

FIG. 8B shows the same image as in FIG. 8A however showing the cross-section near tracheal lumen distal end 114 of tube 100. Most preferably at tracheal lumen distal end 114 image sensor lumen 150L is provided with a lumen having a larger radius than that provided at the proximal end 102 as shown in FIG. 8A. Most preferably tube 100 is expanded about distal end 104 and image sensor lumen 150L to accommodate image sensor arrangement 150. Optionally image sensor lumen 150L about the external surface of tube 110 is widened and/or expanded 1.5 mm to 5 mm from distal end 114 of tracheal lumen 110.

Optionally the image sensor lumen 150L is provided with an notch 150n disposed 22.5 mm from the proximal end 102 of tube 100 and an exit notch having a diameter of about 1.5 mm.

Figure 9:
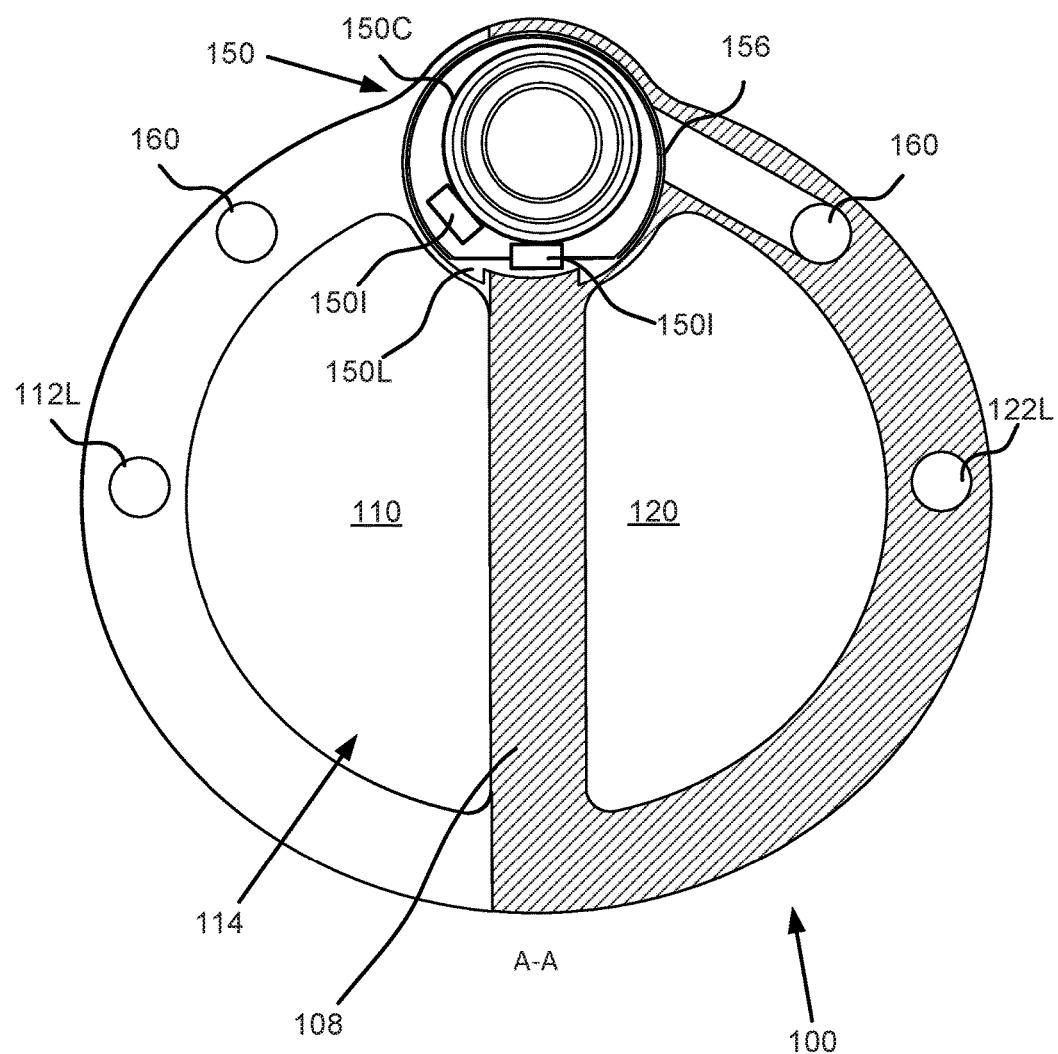
FIG. 9 shows a close up view of the image sensor with integrated light source within a dedicated lumen disposed within the wall of the endobronchial tube according to an optional embodiment of the present invention.

FIG. 9 shows a close up cross sectional bottom-up view (along viewing axis A-A, shown in FIG. 10) of the image sensor arrangement 150 within dedicated image sensor lumen 150L disposed within the wall of the endobronchial tube 100, showing image sensor 150c optionally and preferably provided in the form of a charged-coupled device ("CCD") or a complementary metal-oxide semiconductor ("CMOS"), or the like, and illumination source 150I most preferably provided in the form of at least one and more preferably at least two or more LED, as shown.

While the invention has been illustrated primarily with reference to a left bronchi endobronchial tube, it will be appreciated that the present invention is not limited to a left bronchi endobronchial tube where the inventive and novel aspects equally covers a right bronchi endobronchial tube.

While the invention has been described with respect to a limited number of embodiments, it will be appreciated that many variations, modifications and other applications of the invention may be made.

What is claimed is:

1. An endobronchial tube comprising:
   a tube having a wall;
   a first lumen having a longitudinal portion and an open distal end;
   a first inflatable cuff located proximally of the open distal end of the first lumen;
   a second lumen having an open distal end;
   a second inflatable cuff located distally of the first lumen;
   a dedicated image sensor lumen in the wall comprising a circular cross-section at its distal end;
   an image sensor adjacent an illumination source, the image sensor and the illumination source disposed entirely within the dedicated image sensor lumen at the distal end thereof and having a cross-section that fits entirely within the circular cross-section of the distal end of the dedicated image sensor lumen, within the wall of the tube; and
   a dedicated cleaning nozzle arrangement wholly embedded in the wall of the tube, the dedicated cleaning nozzle arrangement comprising a longitudinal cleaning lumen disposed parallel with the dedicated image sensor lumen and angled portions fluidly coupled to and extending from the longitudinal cleaning lumen, each of the angled portions defining a cleaning nozzle consisting of an elongate aperture in the wall of the tube, connecting to and extending from the longitudinal cleaning lumen to an opening on a surface across a thickness of the wall, the surface being distal of the image sensor and substantially parallel to the longitudinal axis of the tube, thus the cleaning nozzles are arranged distally from the image sensor, wherein the cleaning nozzles comprise a first cleaning nozzle and a second cleaning nozzle, and whereby the dedicated cleaning nozzle arrangement is configured to flush a fluid through the cleaning nozzles to clear a field of view of the image sensor.

2. The endobronchial tube of claim 1, wherein a diameter of the first cleaning nozzle is larger than a diameter of the second cleaning nozzle.

3. The endobronchial tube of claim 2, wherein the diameter of the first cleaning nozzle is about 0.8 mm and the diameter of the second cleaning nozzle is about 0.6 mm.

4. The endobronchial tube of claim 1, wherein the first cleaning nozzle and the second cleaning nozzle each have a diameter from about 0.1 mm to about 2 mm.

5. The endobronchial tube of claim 1, wherein the second cleaning nozzle comprises a plurality of cleaning nozzles.

6. The endobronchial tube of claim 5, wherein the plurality of cleaning nozzles are positioned distally of the first cleaning nozzle.

7. The endobronchial tube of claim 6, wherein the plurality of cleaning nozzles are arranged in a linear fashion about a longitudinal axis of the cleaning lumen.

8. The endobronchial tube of claim 6, wherein the plurality of cleaning nozzles are arranged in an arc.

9. The endobronchial tube of claim 1, wherein the dedicated image sensor lumen is disposed within the wall of the tube between the first lumen and the second lumen.

10. The endobronchial tube of claim 1, wherein the second lumen comprises a second image sensor.

11. The endobronchial tube of claim 1, wherein the second inflatable cuff is located at a distal end of the endobronchial tube.

12. The endobronchial tube of claim 1, wherein the second inflatable cuff is angled toward the longitudinal cleaning lumen.

13. The endobronchial tube of claim 12, wherein the second inflatable cuff is dimensioned to be positioned in and to completely block either a right or left bronchus when inflated.

14. The endobronchial tube of claim 1, wherein the image sensor lumen is configured to provide an image of a tracheal bifurcation of a Tracheal Carina, an opening of a Left Bronchial branch, or an opening of a Right Bronchial branch.

15. The endobronchial tube of claim 1, wherein the cleaning nozzles are aimed proximally toward the image sensor to clear the field of view of the image sensor.

16. The endobronchial tube of claim 1, wherein at least one of the angled portions of the dedicated cleaning lumen include an open end extending through a surface of a wall forming the image sensor lumen thereby defining its respective cleaning nozzle.

* * * * *